US010864166B2

(12) United States Patent
Venkatesh et al.

(10) Patent No.: US 10,864,166 B2
(45) Date of Patent: Dec. 15, 2020

(54) DRUG DELIVERY SYSTEMS COMPRISING SOLID SOLUTIONS OF WEAKLY BASIC DRUGS

(71) Applicant: ADARE PHARMACEUTICALS, INC., Lawrenceville, NJ (US)

(72) Inventors: Gopi Venkatesh, Vandalia, OH (US); Luigi Boltri, Agrate Brianza (IT); Italo Colombo, Treviglio (IT); Jin-Wang Lai, Springboro, OH (US); Flavio Fabiani, Merate (IT); Luigi Mapelli, Milan (IT)

(73) Assignee: Adare Pharmaceuticals, Inc., Lawrenceville, NJ (US)

( * ) Notice: Subject to any disclaimer, the term of this patent is extended or adjusted under 35 U.S.C. 154(b) by 285 days.

(21) Appl. No.: 13/911,961

(22) Filed: Jun. 6, 2013

(65) Prior Publication Data

US 2014/0050797 A1 Feb. 20, 2014

Related U.S. Application Data

(63) Continuation of application No. 11/847,219, filed on Aug. 29, 2007, now abandoned.

(60) Provisional application No. 60/841,760, filed on Aug. 31, 2006, provisional application No. 60/841,893, filed on Aug. 31, 2006.

(51) Int. Cl.
| | |
|---|---|
| *A61K 9/50* | (2006.01) |
| *A61K 31/4406* | (2006.01) |
| *A61K 31/4422* | (2006.01) |
| *A61K 31/454* | (2006.01) |
| *A61K 31/5513* | (2006.01) |

(52) U.S. Cl.
CPC .......... *A61K 9/5026* (2013.01); *A61K 9/5005* (2013.01); *A61K 9/5042* (2013.01); *A61K 9/5047* (2013.01); *A61K 9/5078* (2013.01); *A61K 9/5089* (2013.01); *A61K 31/4406* (2013.01); *A61K 31/4422* (2013.01); *A61K 31/454* (2013.01); *A61K 31/5513* (2013.01)

(58) Field of Classification Search
CPC .. A61K 9/5026; A61K 9/5089; A61K 9/5042; A61K 31/4422; A61K 31/5513; A61K 9/5047; A61K 9/5078; A61K 9/5005; A61K 31/4406; A61K 31/454; A61P 9/12; A61P 9/10; A61P 25/18; A61P 25/08

See application file for complete search history.

(56) References Cited

U.S. PATENT DOCUMENTS

| | | | |
|---|---|---|---|
| 6,500,454 B1 | 12/2002 | Percel et al. | |
| 6,627,223 B2 * | 9/2003 | Percel .................. | A61K 9/5073 424/457 |
| 6,663,888 B2 | 12/2003 | Percel et al. | |
| 2001/0046964 A1 | 11/2001 | Percel et al. | |
| 2003/0113374 A1 | 6/2003 | Percel et al. | |
| 2004/0258749 A1 | 12/2004 | Guldner et al. | |
| 2005/0232988 A1 * | 10/2005 | Venkatesh et al. ........... | 424/464 |
| 2006/0057199 A1 | 3/2006 | Venkatesh et al. | |
| 2006/0073200 A1 | 4/2006 | Leonardi et al. | |
| 2006/0165788 A1 | 7/2006 | Abramowitz et al. | |
| 2006/0165789 A1 | 7/2006 | Abramowitz et al. | |
| 2008/0069878 A1 | 3/2008 | Venkatesh et al. | |

FOREIGN PATENT DOCUMENTS

| | | |
|---|---|---|
| EP | 1123700 B1 | 5/2004 |
| JP | 1-22245 B | 4/1989 |
| JP | H08-208476 A | 8/1996 |
| JP | 9/104620 A | 4/1997 |
| JP | 2000-191519 A | 7/2000 |
| JP | 2002-528485 A | 9/2002 |
| JP | 2003-522141 A | 7/2003 |
| JP | 2004-339071 A | 12/2004 |
| JP | 2005-508922 A | 4/2005 |
| WO | WO 2005/053689 A2 | 6/2005 |

OTHER PUBLICATIONS

Industrial Drug Technology Ed. by Choueshov V. I Kharkov, 2002, vol. 2. p. 383-392 (Chapter 15)—in Russian).
Communication from the Intellectual Property Office of New Zealand for corresponding New Zealand Patent Application No. 575171 (dated Jul. 5, 2010).
Communication from the Russian Patent Office for corresponding Russian Patent Application No. 2009111588/15 (translation) (dated Sep. 14, 2010).
International Search Report based on International Application No. PCT/US07/77153 (dated Jun. 13, 2008).
Supplementary European Search Report, 7 pages, EP appl. No. 07814553.9 (dated Mar. 22, 2013).
Venkatesh, Gopi, "Development of Controlled-Release SK&F 82526-J Buffer Bead Formulations with Tartaric Acid as the Buffer," Pharmaceutical Development and Technology, 3(4), 477-485 (1998).
Written Opinion for Singapore Patent Application No. 20090110-1 dated Apr. 6, 2010.

* cited by examiner

*Primary Examiner* — David J Blanchard
*Assistant Examiner* — Thurman Wheeler
(74) *Attorney, Agent, or Firm* — Cooley, LLP

(57) ABSTRACT

The present invention is directed to pharmaceutical compositions and dosage forms comprising TPR beads, wherein said TPR beads comprise a solid dispersion of at least one active pharmaceutical ingredient in at least one solubility-enhancing polymer, and a TPR coating comprising a water insoluble polymer and an enteric polymer, wherein the active pharmaceutical ingredient comprises a weakly basic active pharmaceutical ingredient having a solubility of not more than 100 μg/mL at pH 6.8.

19 Claims, 11 Drawing Sheets

(A)

(B)

(C)

(D)

(A)

(B)

(A)

(B)

(A)

(B)

(A)

(B)

Drug Release Profiles of TPR Beads

Drug Release Profiles of TPR Beads

DRUG DELIVERY SYSTEMS COMPRISING SOLID SOLUTIONS OF WEAKLY BASIC DRUGS

CROSS-REFERENCE TO RELATED APPLICATIONS

This application claims the benefit of U.S. provisional application No. 60/841,760 and 60/841,893, both filed Aug. 31, 2006, each of which is herein incorporated by reference in its entirety for all purposes.

TECHNICAL FIELD

The present invention relates to modified-release compositions with improved bioavailability, and methods of making such compositions. The compositions of the present invention comprise solid dispersions of at least one active pharmaceutical ingredient and a timed pulsatile release coating.

BACKGROUND OF THE INVENTION

Many therapeutic agents are most effective when made available at constant rates, at or near the absorption sites. The absorption of therapeutic agents made available in this manner generally results in desired plasma concentrations leading to maximum efficacy, and minimum toxic side effects. However, it is often difficult to develop oral pharmaceutical dosage forms which deliver the desired plasma concentrations of the therapeutic agent at constant rates due to the complexity of the absorption process, the many inter-related compositional variables which affect the rate of release of the therapeutic agent from the dosage form, and the physicochemical properties of the therapeutic agent itself. For example, while an orally administered pharmaceutical dosage form passes through the human digestive tract, the drug should be released from the dosage form and be available in solution form at or near the site for absorption from the gastrointestinal (GI) tract. The dosage form—and hence the therapeutic agent—is subjected to varying pHs during transit of the GI tract, i.e., pH's varying from about 1.2 (stomach pH during fasting) to pH's as high as 4.0 (upon consumption of food) or about 7.4 (bile pH: 7.0-7.4 and intestinal pH: 5 to 7). Moreover, the transit time of a dosage form in individual parts of the digestive tract may vary significantly depending on the size of the dosage form and prevailing local conditions (e.g., permeability changes along the GI tract; the properties of luminal contents such as pH, surface tension, volume, agitation, and buffer capacity; and changes following the ingestion of food). The physicochemical properties of the drug substance itself which affect plasma concentrations include its pKa, solubility and crystalline energy, and the compositional properties of e.g., multiparticulate dosage forms, including the size or specific surface area of the drug-containing particles etc. Consequently, it is often difficult to achieve drug release at constant rates.

In addition, basic and acidic drugs exhibit pH-dependent solubility profiles varying by more than 2 orders of magnitude in the physiological pH range. Of these, the most difficult drugs to formulate are weakly basic compounds which are practically insoluble at pH >5 (e.g., have a solubility of 50 µg/mL or less) and require high doses (e.g., an optimum daily dose of 10 mg or larger) to be therapeutically effective. At such high doses, some of the dissolved drug may precipitate upon entering into the pH environment of the gastrointestinal (GI) tract unless the rate of absorption is faster than the rate of drug release. Alternatively, the drug may remain in the supersaturated solution state, for example facilitated by the presence of bile salts and lecithin in the gut, at levels of supersaturation well over an order of magnitude higher than the aqueous solubility are known. However, supersaturated solutions can precipitate, and there is evidence that redissolution and absorption of the drug can then occur at a slower rate. In order to resolve these problems, different approaches have been developed to increase the solubility of the weakly basic drugs, for example, the inclusion of organic acids to form acid addition compounds, or the use of solid dispersions or solid solutions.

However, such approaches are not entirely satisfactory because the solubility of the drugs varies with the physiochemical properties of the drug itself, as well as the method of preparing the pharmaceutical formulation. For example, some weakly basic drugs, such as nifedipine or lercanidipine, do not show significant solubility enhancement in saturated organic acid solutions, and solid dispersions tend to provide an undesirable immediate release of the drug upon oral ingestion.

The compositions of the present invention provide improved delivery of weakly basic therapeutic agents (e.g., with a pKa of less than 14, and which require high doses to maintain target plasma concentrations) with drug release profiles suitable for once-daily dosing regimens.

SUMMARY OF THE INVENTION

In one embodiment, the present invention is directed to a pharmaceutical composition comprising TPR beads, wherein said TPR beads comprise a solid dispersion of at least one active pharmaceutical ingredient and at least one solubility-enhancing polymer; and a TPR coating comprising a water insoluble polymer and an enteric polymer; wherein the active pharmaceutical ingredient comprises a weakly basic active pharmaceutical ingredient having a solubility of not more than 100 µg/mL at pH 6.8.

In another embodiment, the present invention is directed to a method of preparing a pharmaceutical composition, comprising dissolving an active pharmaceutical ingredient and sufficient solubility-enhancing polymer in a pharmaceutically acceptable solvent; removing the pharmaceutically acceptable solvent from the solution of active pharmaceutical ingredient and solubility-enhancing polymer, whereby particles of a solid dispersion of the active pharmaceutical ingredient in the solubility-enhancing polymer are formed; dissolving a water insoluble polymer and an enteric polymer in a pharmaceutically acceptable coating solvent, thereby forming a TPR coating solution; coating the solid dispersion with the TPR coating solution; removing the coating solvent, thereby forming TPR beads comprising a TPR coating formed on the solid dispersion.

DETAILED DESCRIPTION OF THE INVENTION

Figure 1:
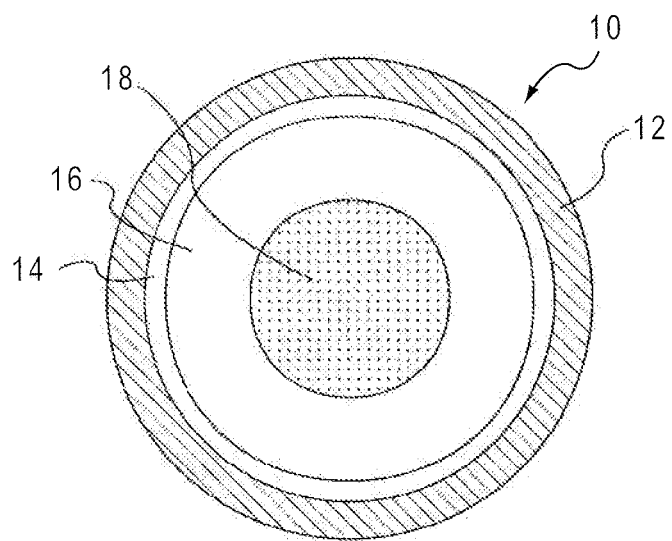
FIG. 1 illustrates a cross-section of one embodiment of a TPR bead of the present invention.

The present invention is directed to pharmaceutical compositions comprising the combination of a solid dispersion of at least one active pharmaceutical ingredient and at least one solubility-enhancing polymer, with a timed pulsatile release (TPR) coating comprising a water-insoluble polymer and an enteric polymer, wherein the active pharmaceutical ingredient comprises a weakly basic active pharmaceutical ingredient having a solubility of not more than 100 µg/mL at pH 6.8. The combination of the solid dispersion of a weakly basic active pharmaceutical ingredient and the TPR coating provides an improved release profile compared to the release profile obtained by conventional compositions in which the weakly basic active pharmaceutical ingredient is not present in the form of a solid dispersion and/or which lacks a TPR coating. For example, by suitable manipulation of the composition comprising at least one TPR coating the release rate can be made to be approximately constant over 12-18 hours, or the time to maximum release rate can be delayed relative to using the solubility-enhancing polymer alone.

The terms "solid dispersion" or "solid solution" refer to a substantially amorphous active pharmaceutical ingredient dispersed in a polymeric matrix, and/or more particularly, at least one active pharmaceutical ingredient and at least one crystallization-inhibiting polymer are substantially molecularly dispersed in the solid state. The term "substantially amorphous" means that less than 40% of the active pharmaceutical ingredient forms a separate crystalline phase in the polymeric matrix. In other embodiments, "substantially amorphous" means that less than 30%, less than 20%, less than 10%, less than 5%, or less than 1% of the active pharmaceutical ingredient forms a separate crystalline phase in the polymeric matrix. Alternatively stated, at least 60%, at least 70%, at least 80%, at least 90%, at least 95%, or at least 99% of the active pharmaceutical ingredient is in the amorphous state. The term "substantially molecularly dispersed" means that less than 40% of the active pharmaceutical ingredient forms a separate crystalline phase in the polymeric matrix, and the remainder of the active pharmaceutical ingredient is dissolved in the polymeric matrix. In other embodiments, "substantially molecularly dispersed" means that less than 30%, less than 20%, less than 10%, less than 5%, or less than 1% of the active pharmaceutical ingredient forms a separate crystalline phase in the polymeric matrix. The solid dispersions of the present invention include combinations of "substantially molecularly dispersed" and "substantially amorphous" active pharmaceutical ingredient in the polymeric matrix, provided that no more than 40% of the active pharmaceutical ingredient, and in some embodiments or more than 30%, no more than 20%, or more than 10%, no more than 5%, or no more than 1% of the active pharmaceutical ingredient forms a crystalline phase in the polymeric matrix.

The term "active pharmaceutical ingredient" can be used interchangeably with the term "drug", "therapeutic agent", etc. As used herein, the term "weakly basic pharmaceutically active ingredient", as well as reference to any specific drug, includes the base, pharmaceutically acceptable salts, polymorphs, stereoisomers, solvates, esters and mixtures thereof. In one embodiment, the weakly basic active pharmaceutical ingredient of the compositions of the present invention can refer to a compound having a pKa of less than 14. In another embodiment, the weakly basic active pharmaceutical ingredient has a solubility of not more than about 100 µg/mL at pH 6.8. In another embodiment, the weakly basic active pharmaceutical ingredient includes at least one basic nitrogen atom. In yet another embodiment, the weakly basic active pharmaceutical ingredient has a pKa of less than 14, and a solubility of not more than about 100 µg/mL at pH 6.8. In yet another embodiment, the weakly basic active pharmaceutical ingredient has a pKa of less than 14, and includes at least one basic nitrogen atom. In yet another embodiment, the weakly basic active pharmaceutical ingredient as a pKa of less than 14, a solubility of not more than 100 µg/mL at pH 6.8, and includes a least one basic nitrogen atom.

As used herein, the terms "solubility-enhancing polymer" or "crystallization-inhibiting polymer" refers to a water-soluble polymer capable, at suitable concentrations, of forming a solid dispersion, as defined herein, of a weakly basic drug in the solubility-enhancing polymer, for example by first dissolving both the drug and polymer in the same solvent system, and then removing the solvent under appropriate conditions. The weakly basic drug is maintained substantially as a molecular dispersion, or in amorphous form during storage, transportation, and commercial distribution of the composition containing the solid dispersion of the solubility-enhancing polymer and weakly basic drug.

As used herein, the term "immediate release" (IR) refers to release of greater than about 75%, in other embodiments greater than about 85% of the active pharmaceutical ingredient in one hour following administration of the composition. The amount of release can be measured in vivo, or in vitro (using conventional USP methods as described herein).

The term "IR beads" refers to particles comprising the active pharmaceutical ingredient, which have immediate release properties. IR beads can include any kind of particles comprising the pharmaceutically active ingredient, e.g. particles of a solid dispersion of the active pharmaceutical ingredient in a solubility-enhancing polymer, or an inert core coated with a solid dispersion of the active pharmaceutical ingredient in a solubility-enhancing polymer. IR beads also include particles comprising the solid dispersion, and further coated with a sealant or protective layer, and which has immediate release properties as described herein.

As used herein, the term "rapidly dispersing microgranules" refers to agglomerated particles comprising primary particles of a sugar alcohol (e.g., D-mannitol) and/or a saccharide (e.g., lactose) in combination with a disintegrant.

The terms, "lag-time membrane coating", "lag-time polymer coating", "timed, pulsatile release (TPR) membrane coating", "TPR polymer coating", or TPR coating, which are interchangeably used in the present application, refer to a coating comprising a water-insoluble polymer in combination with an enteric polymer.

The term, "timed, pulsatile release (TPR) beads" or simply "TPR beads" refers to a particle comprising the active pharmaceutical ingredient, coated with a TPR coating. In some embodiments, TPR beads refer to IR beads coated with a TPR coating, and the release of the weakly basic pharmaceutically active ingredient from TPR beads prepared in accordance with certain embodiments of the present invention is characterized by a sustained-release profile following a short lag-time.

The term "lag-time" refers to a time period wherein less than about 10%, more particularly less than about 5%, more particularly substantially 0%, of the active pharmaceutical ingredient is released, and a lag-time of up to about 4 hours, can be achieved by the TPR coatings of the present invention comprising a combination of water-insoluble and enteric polymers (e.g., Eudragit RL and L polymers).

As used herein, the terms "solubility-modulating organic acid" or "organic acid" refer to a water-soluble, pharmaceutically acceptable organic acid which is capable of increasing the rate and/or the extent of dissolution of the active pharmaceutical ingredient in an aqueous solution of the organic acid.

The term "release rate" refers to the quantity of drug released in vitro or in vivo from a composition per unit time. The units of quantity are often expressed as, e.g., % of the total dose.

The terms "plasma profile", "plasma concentration", "$C_{max}$", or "$C_{min}$" are intended to refer to the concentration of drug in the plasma of a subject, generally expressed as mass per unit volume, typically nanograms per milliliter (ng/mL).

The term "therapeutically effective amount" refers to the amount of active pharmaceutical ingredient necessary to provide the desired pharmacologic result. In practice, the therapeutically effective amount will vary widely depending on the severity of the disease condition, age of the subject, and the desired therapeutic effect.

The pharmaceutical compositions of the present invention comprise a solid dispersion of at least one active pharmaceutical ingredient and at least one solubility-enhancing polymer and a TPR coating.

Specific embodiments of the invention will be described in further detail with reference to the accompanying FIG. 1. FIG. 1 represents a TPR bead 10. The inert particle core 18, the amorphous layer 16 comprising the weakly basic drug, a crystallization-inhibiting polymer (also referred to as solubility-enhancing polymer), and a solubility-enhancing organic acid, the protective seal-coating layer 14, and the lag-time (also referred to as TPR or pulsatile-release) coating 12 make up the TPR bead 10.

Suitable active pharmaceutical ingredients for the pharmaceutical compositions of the present invention include weakly basic drugs. In one embodiment, the active pharmaceutical ingredient has a pKa value of less than 14. In another embodiment, the active pharmaceutical ingredient has a solubility of not more than about 100 µg/mL at pH 6.8. In another embodiment, the active pharmaceutical ingredient has an elimination half life of about 3 hours or longer. In another embodiment, the active pharmaceutical ingredient has a solubility of not more than 50 µg/mL at pH 6.8. In another embodiment, the active pharmaceutical group ingredient has a ratio of optimal daily dose (in mg) to solubility at pH 6.8 (in mg/mL) of at least 100. In yet another embodiment, the active pharmaceutical ingredient has a PKa value of less than 14, a solubility of not more than about 100 µg/mL at pH 6.8, and an elimination half-life of about 3 hours or longer. In yet another embodiment, the active pharmaceutical ingredient has a solubility of not more than about 100 µg/mL at pH 6.8 and a ratio of optimal daily dose (in mg) to solubility at pH 6.8 (in mg/mL) of at least 100. In yet another embodiment, the active pharmaceutical ingredient has a solubility of not more than about 50 µg/mL at pH 6.8 and a ratio of optimal daily dose (in mg) to solubility at pH 6.8 (in mg/mL) of at least 100.

Non-limiting examples of classes of suitable active pharmaceutical ingredients include, but are not limited to analgesics, antihypertensives, antianxiety agents, anticlotting agents, anticonvulsants, anti-diabetic agents, blood glucose-lowering agents, decongestants, antihistamines, anti-inflammatory agents, antitussives, antineoplastics, beta blockers, anti-rheumatic agents, anti-inflammatories, antipsychotic agents, cognitive enhancers, anti-atherosclerotic agents, antiobesity agents, anti-impotence agents, anti-infective agents, anti-infective agents, hypnotic agents, anti-Parkinsonism agents, anti-Alzheimer's disease agents, anti-depressants, and antiviral agents, glycogen phosphorylase inhibitors, cholesterol ester transfer protein inhibitors, CNS (central nervous system) stimulants, dopamine receptor agonists, anti-emetics, gastrointestinal agents, psychotherapeutic agents, opioid agonists, opioid antagonists, anti-epileptic drugs, histamine $H_2$ antagonists, anti-asthmatic agents, smooth muscle relaxants, and skeletal muscle relaxants.

Specific examples of analgesics include acetominophen, rofecoxib, celecoxib, morphine, codeine, oxycodone, hydrocodone, diamorphine, pethidine, tramadol, buprenorphene; antihypertensives include prazosin, nifedipine, lercanidipine, amlodipine besylate, trimazosin and doxazosin; specific examples of antianxiety agents include hydroxyzine hydrochloride, lorazepam, buspirone hydrochloride, pazepam, chlordiazepoxide, meprobamate, oxazepam, trifluoperazine hydrochloride, clorazepate dipotassium, diazepam; specific examples of anticlotting agents include abciximab, eptifibatide, tirofiban, lamifiban, clopidogrel, ticlopidine, dicumarol, heparin, and warfarin; specific examples of anticonvulsants include phenobarbital, methylphenobarbital, clobazam, clonazepam, clorezepate, diazepam, midazolam, lorazepam, felbamate, carbamezepine, oxcarbezepine, vigabatrin, progabide, tiagabine, topiramate, gabapentin, pregabaln, ethotoin, phenyloin, mephenyloin, fosphenyloin, paramethadione, trimethadione, ethadione, beclamide, primidone, brivaracetam, levetiracetam, seletracetam, ethosuximide, phensuximide, mesuximide, acetazolamide, sulthiame, methazolamide, zonisamide, lamotrigine, pheneturide, phenacemide, valpromide, and valnoctamide; specific examples of antidiabetic agents include repaglinide, nateglinide, metformin, phenformin, rosiglitazone, pioglitazone, troglitazone, miglitol, acarbose, exanatide, vildagliptin, and sitagliptin; specific examples of blood glucose-lowering agent include tolbutamide, acetohexamide, tolazamide, glyburide, glimepiride, gliclazide, glipizide and chlorpropamide; specific examples of decongestants include pseudoephedrine, phenylephrine, and oxymetazoline; specific examples of antihistamines include mepyramine, antazoline, diphenhydramine, carbinoxamine, doxylamine, clemastine, dimenhydrinate, pheniramine, chlorpheniramine, dexchlorpheniramine, brompheniramine, tripolidine, cyclizine, chlorcyclizine, hydroxyzine, meclizine, promethazine, trimeprazine, cyproheptadine, azatadine, and ketotifen; specific examples of antitussives include dextromethorphan, noscapine, ethyl morphine, and codeine; specific examples of antineoplastics include chlorambucil, lomustine, tubulazole and echinomycin; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; specific examples of beta-blockers include timolol and nadolol; specific examples of antitussives include dextromethorphan, noscapine, ethyl morphine, theobromine, and codeine; specific examples of anti-neoplastics include actinomycin, dactinomycin, doxorubicin, daunorubicin, epirurubicin, bleomycin, plicamycin, and mitomycin; specific examples of beta-blockers include alprenolol, carteolol, levobunolol, mepindolol, metipranolol, nadolol, oxprenolol, penbutolol, pindolol, propranolol, sotalol, timolol, acebutolol, atenolol, betaxolol, bisoprolol, esmolol, metoprolol, nebivolol, carvedilol, celiprolol, labetalol, and butaxemine; specific examples of antirheumatic agents include adalimumab, azathioprine, chloroquine, hydroxychloroquine, cyclosporine, D-penicillamine, etanercept, sodium aurothiomalate, auranofin, infliximab, leflunomide, methotrexate, minocycline, sulfasalazine; specific examples of anti-inflammatories include steroidal and nonsteroidal anti-inflammatory drugs such as hydrocortisone, prednisone, prednisolone, methylprednisolone, dexamethasone, betamethasone, triamcinolone, beclomethasone, aldosterone, acetaminophen, amoxiprin, benorilate, diflunisal, faislamine, diclofenac, aceclofenac, acemetacin, bromfenac, etodolac, indomethacin, nabumetone, sulindac, tolmetin, carprofen, ketorolac, mefenamic acid, phenylbutazone, azaanti-inflammatoriespropazone, matamizole, oxyphenbutazone, sulfinprazone, piroxicam, lornoxicam, meloxicam, tenoxicam, celecoxib, etoricoxib, lumiricoxib, parecoxib, rofecoxib, valdecoxib, and numesulide; specific examples of antipsychotic agents include iloperidone, ziprasidone, olanzepine, thiothixene hydrochloride, fluspirilene, risperidone and penfluridole; a specific example of a cognitive enhancer includes ampakine; specific examples of anti-atherosclerotic, cardiovascular and/or cholesterol reducing agents include atorvastatin calcium, cerivastatin, fluvastatin, lovastatin, mevastatin, pitavastatin, pravastatin, rosuvastatin, and simvastatin; specific examples of antiobesity agents include dexadrine, dexfenfluramine, fenfluramine, phentermine, orlistat, acarbose, and rimonabant; specific examples of anti-impotence agents include sildenafil and sildenafil citrate; specific examples of anti-infective agents such as antibacterial, antiviral, antiprotozoal, antihelminthic and antifungal agents include carbenicillin indanylsodium, bacampicillin hydrochloride, troleandomycin, doxycyline hyclate, ampicillin, penicillin G, azithromycin, oxytetracycline, minocycline, erythromycin, clarithromycin, spiramycin, acyclovir, nelfinavir, virazole, benzalkonium chloride, chlorhexidine, econazole, terconazole, fluconazole, voriconazole, griseofulvin, metronidazole, thiabendazole, oxfendazole, morantel, cotrimoxazole; specific examples of hypnotic agents include alfaxalone and etomidate; specific examples of anti-Parkinsonism agents include levodopa, bromocriptine, pramipexole, ropinirole, pergolide, and selegiline; anticholinergics such as trihexyphenidyl, benztropine mesylate, procyclidine, biperiden, andethopropazine; antihistamines such as diphenhydramine and dorphenadrine; and amantadine; specific examples of anti-Alzheimer's disease agents include donepezil rivastigmine, galantamine, tacrine; specific examples of antibiotics include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, telcoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin; specific examples of anti-depressants include isocarboxazid; phenelzine; tranylcypromine; specific examples of antiviral agents include azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), delavirdine (Rescriptor); specific examples of glycogen phosphorylase inhibitors include [R—(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-o-xypropyl]amide; specific examples of cholesterol ester transfer protein inhibitors include [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]4-[(3,5-Bis-trifluoromethyl-benzyl)-methoxycarbonyl-amino]-2-eth-yl-6-trifluoromethyl-3,4-dihydro-2H-quinoline-1-carboxylic acid isopropyl ester; specific examples of CNS stimulants include caffeine and methylphenidate; specific examples of dopamine receptor agonists include cabergoline and pramipexole; specific examples of antiemetics include dolasetron, granisetron, ondansetron, tropisetron, palonosetron, domperidone, droperidol, dimenhydrinate, haloperidol, chlorpromazine, promethazine, prochlorperizine, metoclopramide, and alizapride; specific examples of gastrointestinal agents include loperamide and cisapride; specific examples of psychotherapeutic agents include chlorpromazine, thioridazine, prochlorperizine, haloperidol, alprazolam, amitriptyline, bupropion, buspirone, chlordiazepoxide, citalopram, clozapine, diazepam, fluoxetine, fluphenazine, fluvoxamine, hydroxyzine, lorezapam, loxapine, mirtazepine, molindone, nefazodone, nortriptyline, olanzepine, paroxetine, phenelzine, quetiapine, risperidone, sertraline, thiothixene, tranylcypromine, trazodone, venlafaxine, and ziprasidone; specific examples of opioid agonists include hydromorphone, fentanyl, methadone, morphine, oxycodone, and oxymorphone; specific examples of opioid antagonists include naltrexone; specific examples of anti-epileptic drugs include sodium valproate, nitrazepam, phenyloin; specific examples of histamine $H_2$ antagonists include famotidine, nizatidine, cimetidine, ranitidine; specific examples of anti-asthmatic agents include albuterol, montelukast sodium; specific examples of smooth muscle relaxants include nicorandil, iloperidone, and clonazepam; and specific examples of skeletal muscle relaxants include diazepam, lorazepam, baclofen, carisoprodol, chlorzoxazone, cyclobenzaprine, dantrolene, metaxalone, orphenadrine, pancuronium, tizanidine, dicyclomine, clonidine, and gabapentin. Each named drug should be understood to include the neutral form of the drug, as well as pharmaceutically acceptable salts, solvates, esters, and prodrugs thereof.

As discussed above, the solubility of some drugs is pH dependent, and can be enhanced by the addition of an organic acid. However, the solubility of other drugs is only slightly affected by the addition of organic acids, as shown below in Tables 1 and 2 and FIG. 2.

Figure 2:
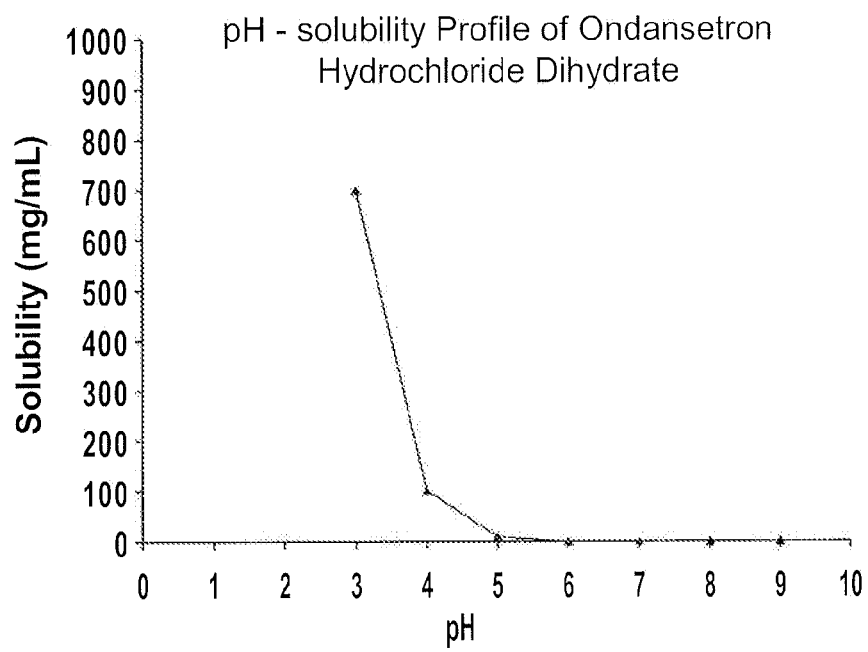
FIG. 2 illustrates pH-solubility profiles for (a) ondansetron hydrochloride, (b) carvedilol, (c) dipyridamole, and (d) clonazepam.
Figure 2:
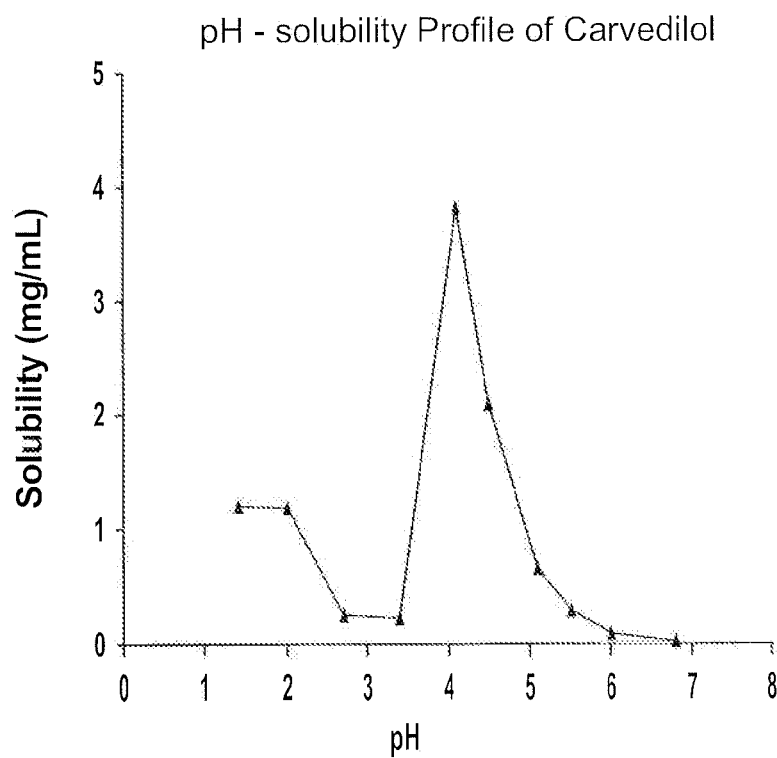
Figure 2:
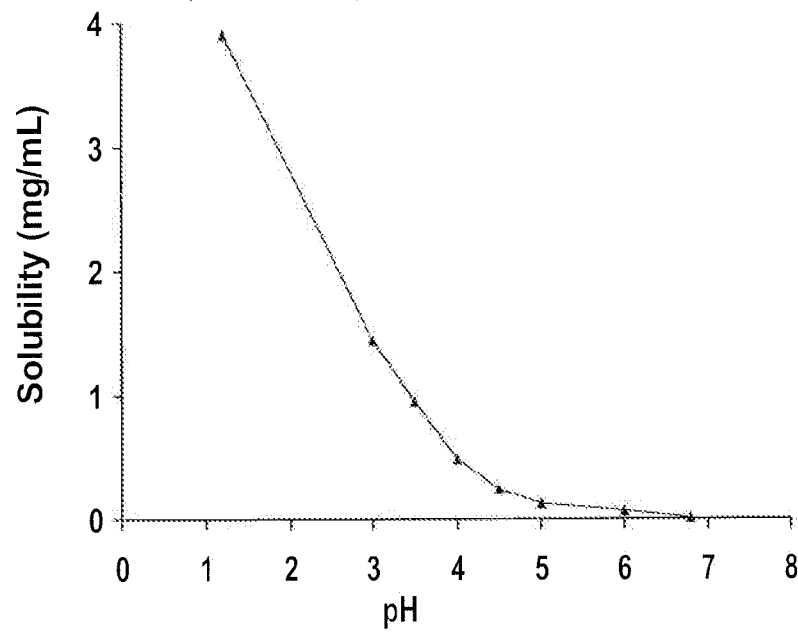
Figure 2:
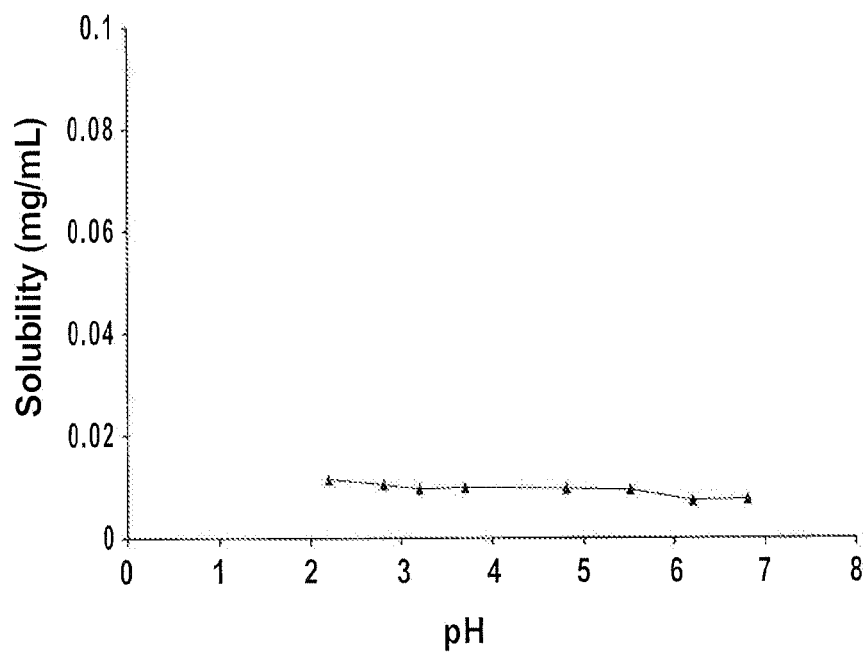

Table 1 lists the solubility enhancement of weakly basic drugs in organic acid buffers (see also FIG. 2). Three distinct groups can be identified. Group A drugs, as represented by ondansetron hydrochloride, exhibit a dramatic increase in solubility of the weakly basic active in a buffer with a trace of fumaric acid. For example, the solubility of ondansetron of about 26 mg/mL in the buffer containing only 0.05 mg/mL of fumaric acid, remains unchanged upon increasing the concentration of fumaric acid in the buffer up to 5 mg/mL. In Group B, represented by dipyridamole, carvedilol, and iloperidone, the solubility of the weakly basic drug increases with increasing concentration of the acid. In Group C, represented by clonazepam, the organic acid has very limited impact, i.e., the solubility enhancement amounts typically to less than 3-fold. For example, the solubilities of clonazepam are about 11.6 and 6.9 µg/mL in buffers at pH 2.3 and 6.8 containing a higher and lower concentration of fumaric acid, respectively.

TABLE 1

Solubilities of Weakly Basic Drugs in Organic Acids

| Concentration of Fumaric Acid (mg/mL) | Start pH | End pH | Solubility of Ondansetron Hydrochloride in Fumaric Acid (mg/mL) | Start pH | Solubility of Dipyridamole in Fumaric Acid (mg/mL) |
|---|---|---|---|---|---|
| 5 | 2.13 | 2.01 | 26.9 | 2.98 | 6.24 |
| 2.5 | 2.26 | 2.14 | 27.0 | 3.42 | 1.80 |
| 1 | 2.48 | 2.40 | 26.1 | 3.68 | 0.93 |
| 0.25 | 2.79 | 2.75 | 26.2 | 3.88 | 0.65 |
| 0.05 | 3.19 | 3.49 | 26.0 | 4.33 | 0.27 |
| 0.01 | 3.64 | 4.05 | 26.1 | 4.71 | 0.13 |
| 0.0025 | 4.15 | 4.33 | 26.1 | 6.28 | 0.006 |

| Solubility (mg/mL) of Carvedilol in Tartaric Acid | | Solubility (mg/mL) of Clonazepam in Fumaric Acid | | Solubility (mg/mL) of Clonazepam in Aspartic Acid | |
|---|---|---|---|---|---|
| pH of Buffer | (mg/mL) | pH of Buffer | (mg/mL) | \pH of Buffer | \(mg/mL) |
| 2.12 | 2.51 | 2.3 | 0.0116 | | |
| 2.28 | 1.36 | 2.8 | 0.0103 | 2.84 | 0.029 |
| 2.54 | 0.731 | 3.2 | 0.0096 | 2.92 | 0.023 |
| 2.94 | 0.508 | 3.7 | 0.0098 | 3.00 | 0.022 |
| 3.64 | 0.121 | 4.8 | 0.0095 | 3.32 | 0.021 |
| 5.46 | 0.105 | 5.5 | 0.0093 | 4.21 | 0.018 |
| 5.90 | 0.028 | 6.2 | 0.0072 | 6.39 | 0.018 |
| | | 6.8 | 0.0069 | | |

TABLE 2

Solubility of Nifedipine in Buffers

| Phosphate Buffer | | Fumaric Acid | | Aspartic Acid | |
|---|---|---|---|---|---|
| pH | µg/mL | pH | µg/mL | pH | µg/mL |
| 4.45 | 5.1 | 2.20 | 7.1 | 2.88 | 5.7 |
| 5.4 | 5.2 | 3.28 | 6.2 | 3.90 | 5.7 |
| 6.52 | 5.2 | 4.24 | 5.6 | 4.84 | 5.3 |
| 7.53 | 5.2 | 5.22 | 5.3 | 5.83 | 5.4 |

In one embodiment of the pharmaceutical compositions of the present invention, the active pharmaceutical ingredient is nifedipine. In another embodiment, the active pharmaceutical ingredient is lercanidipine. It is to be understood, however, that the scope of the present invention is not limited to any particular active pharmaceutical ingredient.

Suitable solubility-enhancing polymers useful in the pharmaceutical compositions of the present invention include but are not limited to polyvinylpyrrolidone (PVP or povidone), copolymers of vinyl acetate/vinylpyrrolidone (e.g. Kollidon VA 64), methylcellulose, hydroxypropyl cellulose, hydroxypropyl methylcellulose (hypromellose), hydroxypropyl methylcellulose acetate succinate (HPMCAS), polyethylene oxide, polyethylene glycol, and cyclodextrin.

The type and amount of solubility-enhancing polymer is selected so that the combination of active pharmaceutical ingredient and solubility-enhancing polymer form a solid dispersion as defined herein. Some of the solubility-enhancing polymers useful for preparing solid solutions/dispersions are conventionally used as binders. However, in order to provide a solid dispersion of the active pharmaceutical ingredient, the ratio of solubility-enhancing polymer to active pharmaceutical ingredient is generally significantly higher than the ratio of polymeric binder to active pharmaceutical ingredient in conventional pharmaceutical formulations. (In conventional pharmaceutical formulations, the ratio of polymeric binder to active pharmaceutical ingredient is typically less than 1/9, for example about 1/50 to about 1/20.) In one embodiment, the ratio of solubility-enhancing polymer to active pharmaceutical ingredient in the solid dispersion ranges from 9/1 to 1/6 (by weight). In another embodiment, the ratio the solubility-enhancing polymer to active pharmaceutical ingredient in the solid dispersion ranges from about 3/1 to about 1/3 (by weight). In yet another embodiment, the ratio the solubility-enhancing polymer to active pharmaceutical ingredient in the solid dispersion ranges from about 2/1 to about 1/2 (by weight), or about 1/1.

The solid dispersion can be in the form of particles (e.g., granules, pellets, beads, and the like), or alternatively can be layered on to an inert core. For example, the active pharmaceutical ingredient and solubility-enhancing polymer can be dissolved in a pharmaceutically acceptable solvent (or mixture of solvents) and coated onto the inert core. Upon removal of the solvent, the solid dispersion is formed as a coating on the inert core. Any pharmaceutically acceptable inert material can be used as an inert core, for example sugar spheres or beads (e.g., Celphere®), cellulose spheres, a silicon dioxide spheres, or the like, with a suitable particle size distribution (e.g. from about 20-25 mesh to 35-40 mesh sugar spheres for making coated beads for incorporation into a capsule formulation and sugar spheres or cellulose spheres having a narrow particle size distribution in the range of about 50-100 mesh for making coated beads for incorporation into an ODT formulation. The thickness of the solid dispersion layer and relative amounts of active pharmaceutical ingredient and solubility-enhancing polymer can be adjusted to provide a therapeutically effective amount of the active pharmaceutical ingredient. For example, the inert cores layered with a solid dispersion of the active pharmaceutical ingredient can contain 2% to about 50% by weight of the active pharmaceutical ingredient (relative to the total weight of the drug-coated inert core).

The solid dispersion of the pharmaceutical compositions of the present invention is coated with a TPR coating comprising a water-insoluble polymer and an enteric polymer, for example the TPR coatings described in U.S. Pat. No. 6,627,223, herein incorporated by reference for all purposes. The TPR coating modulates the release of the active pharmaceutical ingredient to provide a therapeutically effective level of the active pharmaceutical ingredient in the plasma of a patient, e.g. for a 12-24 hour period. In some embodiments, the TPR coating can delay the release of the active pharmaceutical ingredient for a short lag-time (e.g., up to about four hours). In addition, the TPR coating can provide a sustained therapeutic level of the drug over an extended period, e.g. up to about 12, up to about 18, or up to about 24 hours.

Suitable water-insoluble polymers include cellulose derivatives (e.g. ethylcellulose), polyvinyl acetate (Kollicoat SR30D from BASF), neutral copolymers based on ethyl acrylate and methylmethacrylate, copolymers of acrylic and methacrylic acid esters with quaternary ammonium groups, such as Eudragit NE, RS or RS30D, RL or RL30D and the like.

Enteric polymers are insoluble at the low pH levels found in the stomach, but are relatively soluble at the higher pH levels found in the intestinal tract. Suitable enteric polymer include acid substituted cellulose esters (e.g., cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers and shellac. Commercially available enteric polymers are sold under the trade name "Eudragit" (e.g., Eudragit L100, S100, L30D) manufactured by Rhom Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

The ratio of water-insoluble polymer to enteric polymer in the TPR coating can vary from about 1/9 to about 9/1 (by weight). In one embodiment, the ratio of water-insoluble polymer to enteric polymer can vary from about 1/4 to about 4/1, or about 1/3 to about 3/1 (by weight). The total weight of the enteric coating can range from about 5-50% of the total weight of the TPR bead. In one embodiment, the total weight of the TPR coating on the TPR bead ranges from about 10% to about 25% by weight, based on the total weight of the TPR bead.

The enteric and water-insoluble polymers used in forming the TPR coating is can be plasticized. Representative examples of suitable plasticizers that can be used to plasticize the TPR coating layer include triacetin, tributyl citrate, triethyl citrate, acetyl tri-n-butyl citrate, diethyl phthalate, castor oil, dibutyl sebacate, acetylated monoglycerides and the like or mixtures thereof. The plasticizer, when present, can comprise about 3 to 30% of the total weight of the TPR coating. In one embodiment, the plasticizer comprises about 10 to 25% of the total weight of the TPR coating. The type and amount of plasticizer depends on the nature of the water-insoluble and enteric polymers of the TPR layer, and the nature of the coating system (e.g., aqueous or solvent based, solution or dispersion based, and the total solids content of the coating system).

In addition to the solid dispersion (comprising a least one active pharmaceutical ingredient and at least one solubility enhancing polymer) and the TPR coating, the pharmaceutical compositions of the present invention can further comprise additional pharmaceutically acceptable ingredients or excipients. Examples of suitable excipients for use in the compositions or dosage forms of the present invention include fillers, diluents, glidants, disintegrants, binders, lubricants etc. Other pharmaceutically acceptable excipients include acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples of suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents include e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants include e.g. alginic acid or alginates, microcrystalline cellulose, low-substituted hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc.

Specific examples of binders include e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, polyethylene oxides, povidone, pregelatinized starch etc.

Specific examples of glidants and lubricants include stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients include e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

Antioxidants used to improve long term chemical stability of the amorphous solid solution/dispersion include e.g. ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives, etc.

In addition, the pharmaceutical compositions of the present invention can further comprise a pharmaceutically acceptable organic acid. The pharmaceutically acceptable organic acid can further improve or modulate the release profile of the active pharmaceutical ingredient (e.g. rate and extent of release). Suitable pharmaceutically acceptable organic acids useful in the compositions of the present invention include, but are not limited to, citric acid, fumaric acid, aspartic acid, tartaric acid and succinic acid. In some embodiments, the solid dispersion of active pharmaceutical ingredient and solubility enhancing polymer includes at least one pharmaceutically acceptable organic acid in an amount ranging from about 10-90% of the weight of the solid dispersion. In other embodiments, the amount organic acid ranges from 25-75% by weight of a solid dispersion.

The compositions of the present invention can also include one or more additional coating layers (e.g., protective or sealant layers, compressible coatings, enteric layers, taste-masking layers, etc.). For example, the additional coating layer(s) can include one or more protective or sealant coating(s) comprising e.g., Opadry Clear or Pharmacoat 603 (hydroxypropylmethylcellulose coating compositions), or hydroxypropylcellulose, or ethylcellulose. The protective or sealant coating can be applied between the solid dispersion and the TPR coating, on top of the TPR coating, or multiple protective were sealant coatings, e.g. between the solid dispersion in the TPR coating as well as on top of the TPR coating. The additional coating layer(s) can also include a compressible coating, e.g. a layer of highly plasticized ethyl cellulose or hydroxypropylcellulose deposited over IR beads, taste-masked IR beads or TPR beads comprising solid dispersions.

Other embodiments of the pharmaceutical composition of the present invention can include one or more enteric layers comprising one or more enteric polymers as described herein. The optional enteric layers can be deposited between the solid dispersion and the TPR coating, and/or deposited over the TPR coating.

The pharmaceutical compositions of the present invention can include any combination of protective or sealant layers, compressible coatings, and enteric layers which provide the desired handling properties and drug release properties.

The pharmaceutical compositions of the present invention can be formulated into various oral dosage forms, for example capsules (e.g., gelatin or HPMC capsules), tablets, or orally disintegrating tablets (ODT). Tablets differ from ODT dosage forms in that tablets are intended to be swallowed intact and rapidly disperse upon entering the stomach, while ODTs rapidly disintegrate on contact with saliva in the oral cavity, forming a smooth suspension of particles which are easily swallowed.

In some embodiments, the dosage forms of the present invention comprise only TPR beads. In other embodiments, the dosage forms of the present invention can comprise blends of immediate release (IR) beads and TPR beads (i.e., as described herein). IR beads comprise a solid dispersion of the active pharmaceutical ingredient in a solubility-enhancing polymer, and release the active pharmaceutical ingredient essentially immediately (e.g., ≥75% release of the drug within about 60 minutes of administration). IR beads can comprise particles of a solid dispersion, or a solid dispersion of the active pharmaceutical ingredient in a solubility-enhancing polymer "layered" onto an inert core, as described herein. IR beads can also optionally include one or more protective or select layers. The IR beads can then be converted to TPR beads by adding a TPR coating.

When the dosage forms of the present invention comprise blends of IR and TPR beads, the IR beads can be uncoated, optionally coated with a sealant or protective coating, and/or optionally coated with a taste masking layer. The taste masking layer can include e.g. any of the taste masking compositions described in U.S. application Ser. Nos. 11/213,266, 11/248,596, and 11/256,653, each of which is herein incorporated by reference in their entirety. Specifically, suitable taste masking layers comprise one or more pharmaceutically acceptable water-insoluble polymers combined with one or more pore forming agents. Non-limiting examples of suitable pharmaceutically acceptable water-insoluble polymers for the taste masking layer include, e.g. ethylcellulose, cellulose acetate, cellulose acetate butyrate, polyvinyl acetate, and methacrylate polymers (e.g., Eudragit RL, RS, and NE and 30D). Non-limiting examples of suitable pore forming agents include sodium chloride, calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium phosphate, polyvinyl pyrrolidone, crospovidone, Eudragit E100, Eudragit EPO, and mixtures thereof. The ratio of water-insoluble polymer to pore former in the taste masking layer ranges from about 95/5 to about 50/50, or in some embodiments about 85/15 to about 65/35. The amount of taste masking layer applied to the IR bead can range from about 5% to about 50% of the total weight of the coated IR bead, in some embodiments about 10% to about 50% of the total weight of the coated IR bead.

When the dosage forms of the present invention comprise blends of IR and TPR beads, the ratio of IR to TPR beads ranges from about 1/9 to about 5/5, and in some embodiments, from about 1/4 to about 1/1 (by weight).

When pharmaceutical compositions of the present invention are formulated into an ODT dosage form, the compositions further comprise a disintegrant. The disintegrant can be in the form of rapidly dispersing microgranules comprising at least one disintegrant in combination with at least one sugar alcohol and/or saccharide. Non-limiting examples of suitable disintegrants include crospovidone (crosslinked polyvinylpyrrolidone), starch, cellulose, sodium starch glycolate, and sodium carboxymethylcellulose. Non-limiting examples of sugar alcohols include arabitol, erythritol, lactitol, maltitol, mannitol, sorbitol, and xylitol. Non-limiting examples of suitable saccharides include lactose, sucrose, and maltose.

The ratio of the disintegrant to the sugar alcohol and/or saccharide in the rapidly dispersing microgranules ranges from about 1/99 to about 10/90, and in some embodiments is about 5/95 (by weight).

The ratio of coated drug-containing beads (i.e., coated beads comprising the solid solution) to rapidly dispersing microgranules in the ODT dosage form varies from about 1/9 to 1/1 and in some embodiments from about 1:4 to about 1:2.

Since ODT dosage forms disintegrate rapidly in the oral cavity of a patient, the organoleptic properties of the ODT are an important consideration. For example, the ODT should be formulated to provide good "mouthfeel" and taste characteristics. "Mouthfeel" describes how a product feels in the mouth. In order to obtain a "mouthfeel" which is not gritty, the TPR beads, rapidly dispersing microgranules, and optional IR beads should have an average particle size of 400 μm or less, in some embodiments 300 μm or less, and in still other embodiments, 200 μm or less. In one embodiment, the primary particles comprising the rapidly dispersing microgranules (i.e., particles of a disintegrant and sugar alcohol and/or saccharide which are agglomerated to form the rapidly dispersing microgranules) have an average particle size of 30 μm or less, in other embodiments 25 μm or less, and in still other embodiments 20 μm or less.

In one embodiment, and ODT dosage form comprising the composition of the present invention comprises TPR beads and rapidly dispersing microgranules as described herein. The ODT dosage form can further comprise additional excipients, for example compression aids (e.g., microcrystalline cellulose) and/or additional disintegrants (which may be the same or different from the disintegrants of the rapidly dispersing microgranules). The ODT dosage form can also include a lubricant (e.g., magnesium stearate), or may not include lubricants if compressed in externally lubricated die system. In one embodiment, an ODT dosage form of the present invention disintegrates on contact with saliva in the oral cavity in about 60 seconds, forming an easy-to-swallow suspension with good "mouthfeel". In another embodiment, an ODT dosage form of the present invention disintegrates on contact with saliva in the oral cavity in about 30 seconds, forming an easy-to-swallow suspension with good "mouthfeel".

In one embodiment, the TPR beads of the dosage form (e.g., tablet, ODT, or capsule) can comprise an inert core coated with the solid dispersion of drug and solubility enhancing polymer, then coated with a TPR layer, and optionally coated with one or more sealant layers or enteric layers.

When present, the IR beads of the dosage form (e.g., tablet, ODT, or capsule) can comprise an inert core coated with the solid dispersion of drug and solubility enhancing polymer, and optionally coated with a sealant layer and/or taste masking layer as described herein. Such high are beads can also serve as an "intermediate" for preparing TPR beads—when coated with a TPR layer, IR beads are converted to TPR beads.

Alternatively, IR beads can be prepared by forming particles of the solid dispersion (e.g. by spray drying, grinding "bulk" or larger particulate forms of the solid dispersion, or granulating one or more pharmaceutically acceptable excipients (e.g., a filler, binder, disintegrant, etc.) with the solid dispersion, which can then be optionally extruded and spheronized. Such IR particles/beads/pellets can then be converted to TPR beads upon coating with a TPR layer.

The dosage forms of the present invention may include one or more different types of TPR beads (e.g., TPR beads with different TPR layers, or with different combinations of sealant and/or enteric layers). For example, TPR beads having different TPR layers can exhibit different lag time characteristics and/or different release rate characteristics, thereby providing the dosage form with different overall drug release characteristics. It is its forms which include different types of TPR beads can also optionally include IR beads to provide some immediate release characteristics. For example, in one embodiment, a once-daily dosage form comprises a mixture of IR beads (comprising an active pharmaceutical ingredient with an elimination half-life of about 7 hours) which allows immediate release and a second population of TPR beads with a lag-time of up to about 4 hours, which provides a delayed, sustained-release profile of the drug over about 12-20 hours, and maintains therapeutically effective plasma concentrations over about 18-24 hrs.

The solid solution or dispersion of an active pharmaceutical ingredient in the solubility-enhancing polymer can be prepared by dissolving the active pharmaceutical ingredient and the solubility-enhancing polymer in a pharmaceutically acceptable solvent or a mixture of solvents. The solution of active pharmaceutical ingredient and solubility-enhancing polymer is then dried under conditions which promote formation of a solid solution of the active pharmaceutical ingredient in the solubility-enhancing polymer. As discussed above, the formation of a molecularly dispersed solid dispersion is favored by relatively high levels of solubility-enhancing polymer relative to the active pharmaceutical ingredient. In addition, solid dispersions can also be formed by rapidly removing the solvent from the solution of active pharmaceutical ingredient and solubility enhancing polymer, for example by spray drying, or by coating the solution of active pharmaceutical ingredient and solubility-enhancing polymer onto an inert core (forming a drug-layered bead), e.g. using fluidized bed coating methods. Alternatively, solid dispersions can also be prepared by dissolving the active pharmaceutical ingredient into a melt of the solubility-enhancing polymer, e.g. by polymer extrusion methods, such as by compounding in a twin screw extruder. If necessary to obtain a suitable particle size (e.g. a particle size of less than 400 μm for ODT dosage forms), particles of the solid dispersion can optionally be milled (to reduce the particle size), or granulated (e.g. rotogranulation, or granulation followed by extrusion-spheronization) in the presence of suitable excipients. The solid dispersion can also be formed into 1-2 mm diameter "mini-tablets", e.g. formed by compressing particles of the solid dispersion, optionally with excipients such as compression aids, lubricants etc., using round beveled punches of the appropriate dimensions.

In one embodiment, the solid dispersion is prepared by granulating the solubility enhancing polymer, the weakly basic drug and optionally other pharmaceutically acceptable excipients (e.g., binders, diluents, fillers) in a high-shear granulator, or a fluid bed granulator, such as Glatt GPCG granulator, and granulated to form agglomerates. The wet mass from the high-shear granulator can also be extruded and spheronized to produce spherical particles (pellets).

When the solid dispersion is prepared by solvent processing methods, as discussed above, the pharmaceutically acceptable solvent can be a single solvent, or a mixture of solvents. Non-limiting examples of suitable solvents include water, ketones such as acetone, alcohols such as ethanol, and mixtures thereof (e.g., aqueous acetone, 95% ethanol, etc.).

Once prepared, the solid dispersion particles (e.g., spray-dried solid dispersion of drug/polymer, drug-layered beads, granulated solid dispersion, mini-tablets, etc.) may be optionally coated with a protective sealant coat (e.g., Pharmacoat™ 603 or Opadry® Clear).

The solid dispersion particles prepared as described above can be referred to as IR (immediate release) beads or particles, because such beads or particles would substantially immediately release the active pharmaceutical ingredient if administered in this form. The IR beads or particles prepared as described above are then coated with a TPR coating solution comprising a water-insoluble polymer and an enteric polymer dissolved in a pharmaceutically acceptable solvent. Any suitable coating process can be used to apply the TPR coating, for example fluidized bed coating methods, etc.

In some embodiments, it is desirable to apply a plurality of coatings to the IR beads or particles, in addition to the TPR coating. For example, in some embodiments the IR beads are first coated with an enteric coating (e.g. comprising at least one enteric polymer, described herein, dissolved in a pharmaceutically acceptable solvent), dried to remove the coating solvents, then coated with the TPR coating as described above. In other embodiments, the IR beads are coated with an enteric polymer coating, a TPR coating, and then a second enteric polymer coating. In yet other embodiments, the IR beads are coated with a first TPR coating, an enteric polymer coating, and then a second TPR coating, wherein the first and second TPR coatings are independently either the same or different. In still other embodiments, sealant layers (as described herein) are coated onto the IR beads prior to applying the TPR and/or enteric polymer coating layers. In still other embodiments, a sealant layer can be applied after applying the TPR and/or enteric polymer coating layers.

In pharmaceutical dosage forms which contain a mixture of TPR and IR beads, the IR beads can be coated with a taste masking layer. For example, any of the IR beads described herein can be coated with a solution comprising a pharmaceutically acceptable solvent, a water-insoluble polymer, and optionally a pore former, using any suitable coating technique such as fluidized bed coating or coacervation.

Pharmaceutical dosage forms can then be prepared from TPR beads, e.g. by compressing TPR beads into tablets, compressing TPR beads and a disintegrant (e.g. rapidly dispersing microgranules) into an ODT, or filling a capsule with the TPR beads using conventional methods. These pharmaceutical dosage forms can optionally contain additional excipients, as well as IR beads, as described herein. In one embodiment, the composition of the present invention, and optionally additional excipients and/or IR beads, is compressed into tablets using an externally lubricated tablet press. In another embodiment, the composition of the present invention, rapidly disintegrating microgranules, optionally additional excipients and/or IR beads, is compressed into an ODT.

Pharmaceutical dosage forms comprising the compositions of the present invention release therapeutically effective levels of the active pharmaceutical ingredient over a 12-18 hour period, for example as shown in FIGS. 7-12. The drug release profile for compositions work dosage forms of the present invention can be evaluated in vitro using various dissolution testing methods, such as United States Pharmacopoeia Apparatus 1 (baskets @ 100 rpm) or Apparatus 2 (paddles @ 50 rpm) and a two-stage dissolution methodology (testing in 700 mL of 0.1N HCl (hydrochloric acid) for the first 2 hours and thereafter in 900 mL at pH 6.8 obtained by adding 200 mL of a pH modifier). Drug/acid-release with time is determined by HPLC on samples obtained at selected intervals.

In one embodiment, the compositions of the present invention provide a therapeutically effective plasma concentration of the active pharmaceutical ingredient over a period of at least about 12 hours when dissolution tested by United States Pharmacopoeia (USP) dissolution methodology using a two-stage dissolution medium (first 2 hours in 0.1N HCl followed by testing in a buffer at pH 6.8).

In order to assess the type of in vitro release profile needed to achieve a once-daily plasma concentration profile, a modeling exercise is typically performed using the pharmacokinetic parameters for the drug using the software program, WinNonlin™ Standard Version 2.1 or equivalent (e.g., GastroPlus®) to fit a 1-compartment first order model with a lag-time assuming first order elimination kinetics. The primary parameters are then input into another program, Stella Version 6.01 using a previously established model with slight modifications. Different in vitro release profiles are generated, and from target once-daily release profiles, desired in vitro release (medium, target and fast) profiles are generated by deconvolution.

The following non-limiting examples illustrate capsule dosage forms which exhibit one or more drug release "pulses" and a predetermined delayed-onset. The in vitro drug-release profile or the corresponding in vivo plasma concentration profile upon oral administration of the dosage form can be designed to provide the desired profile to achieve maximum therapeutic efficacy and enhance patient compliance (e.g., by providing a once-a-day dosage form) by adjusting the amount or thickness of the TPR layer, and optionally adjusting the number and type of additional layers (e.g., enteric or sealant layers). The dosage forms of the present invention provide improved drug release profiles which maintain drug plasma concentrations at levels which minimize side-effects associated with the drug release profile of conventional dosage forms.

Example 1

Turbidity Measurements

A concentrated solution (3 mL) of lercanidipine hydrochloride in acetone (0.5 mg/ml) was added to 200 mL of a buffer solution (pH 6.0) containing Kollidon VA 64, Methocel E5 (hypromellose), polyethylene glycol (PEG 6000), cyclodextrin or Kollidon 14 PF (polyvinyl pyrrolidone) at the ratio of 1:2 by weight with respect to the polymer. It is evident from FIG. 3A that the drug solutions showed improved stability thus strongly reducing the risk of crystallization of the conjugated base of lercanidipine HCl.

Intrinsic Dissolution Rate Measurements

Figure 4:
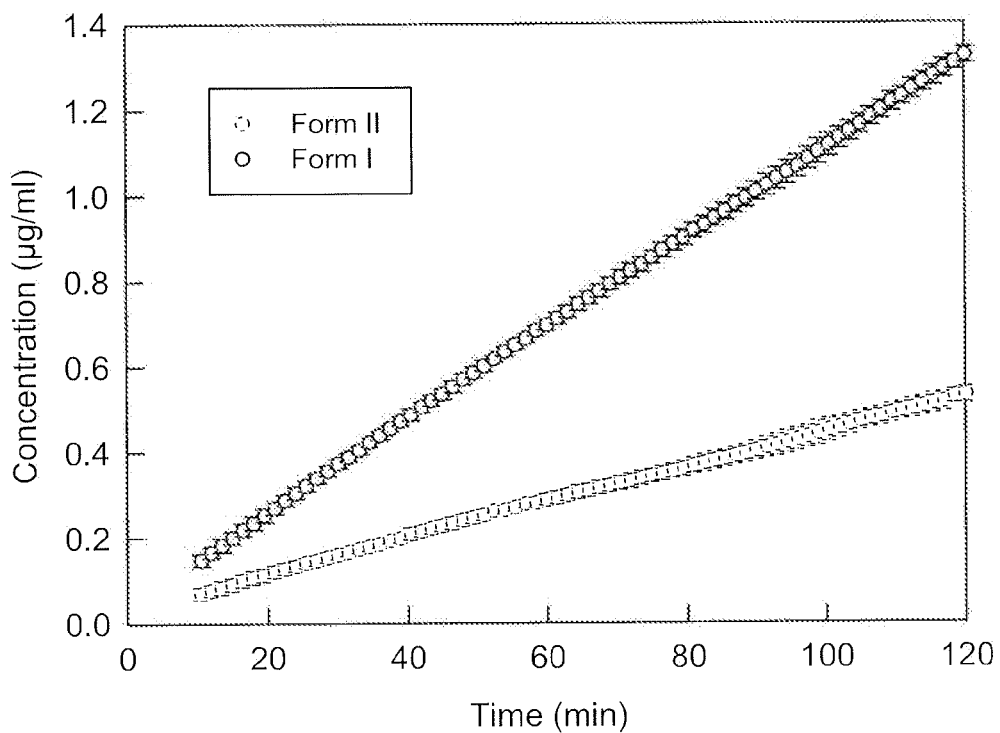
FIG. 4 illustrates intrinsic dissolution rates (IDR) of Lercanidipine HCl—(A) Polymorph I, (B) Polymorph II and (C) Amorphous materials (drug-polymer solid solutions)
Figure 4:
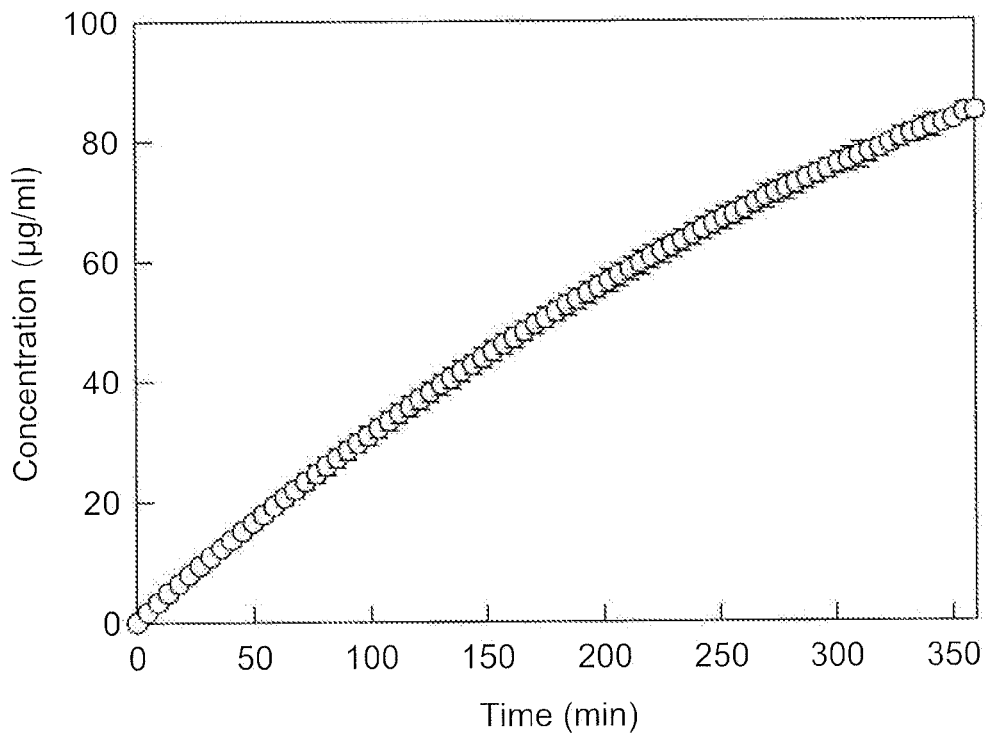

Intrinsic dissolution rates were determined for two different polymorphs of lercanidipine hydrochloride as well as amorphous materials (e.g., amorphous drug and 1:2 solid solutions of lercanidipine hydrochloride with Methocel E5 and Kollidon VA 64). The data are shown in FIG. 4. While the crystalline polymorphs exhibit poor dissolution rates as well as extent of dissolution, the solid solutions exhibit significantly higher dissolution rates as well as extent of dissolution.

Powder X-Ray Diffraction

Figure 5:
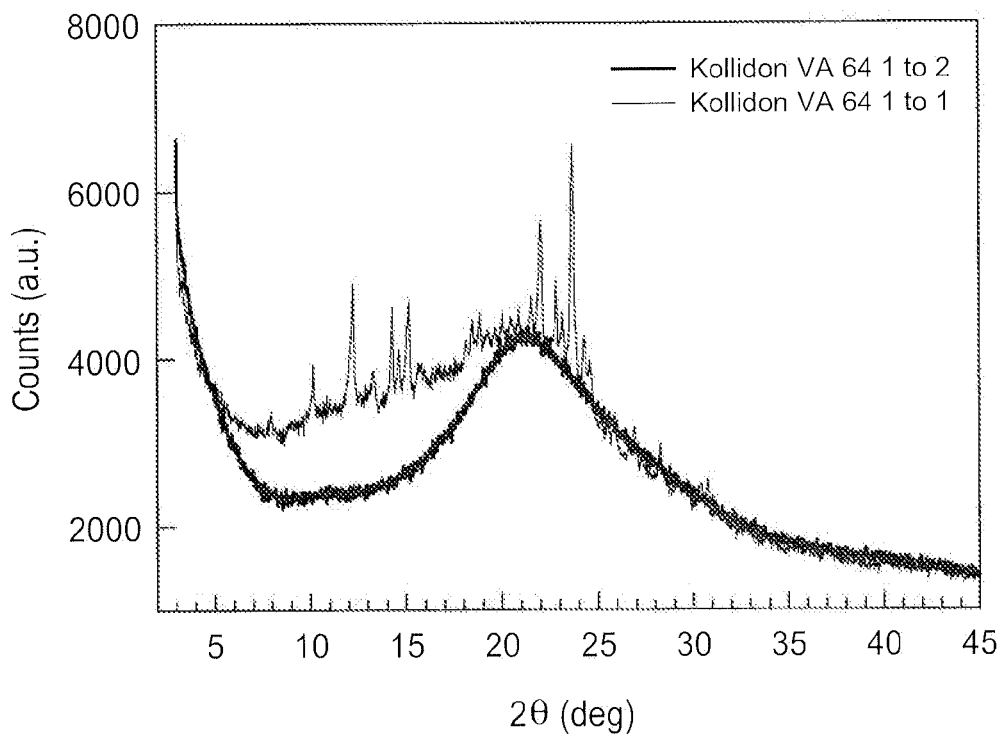
FIG. 5 illustrates the powder X-ray diffraction patterns of solid dispersions of lercanidipine HCl and (A) Kollidon VA 64 or (B) Methocel E5.
Figure 5:
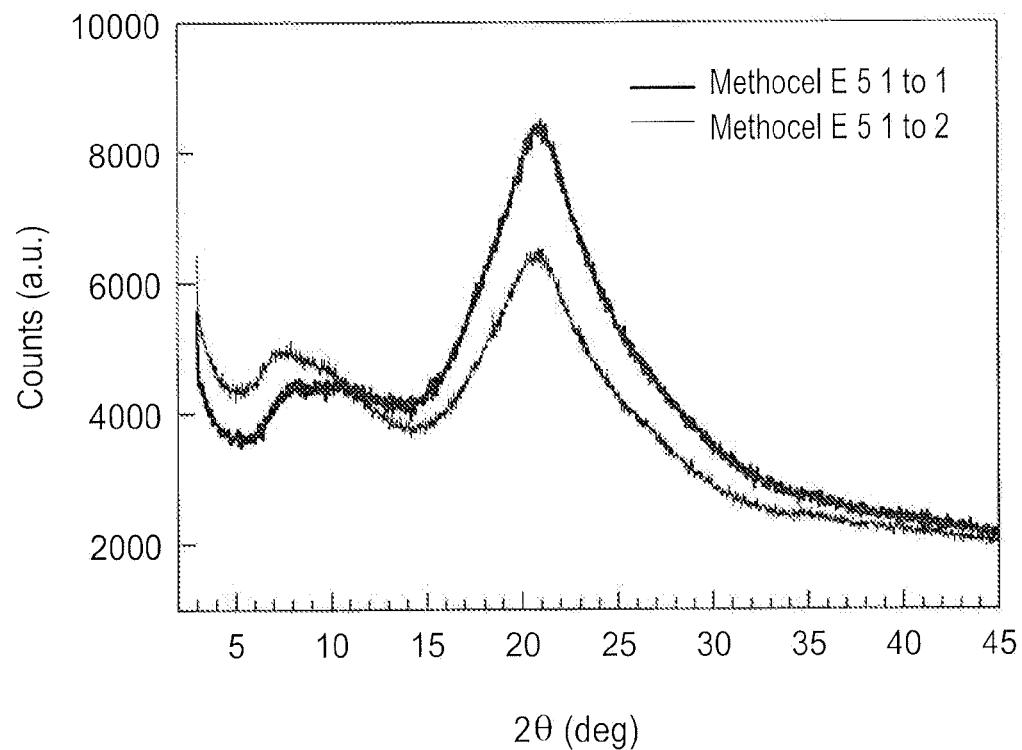

Lercanidipine hydrochloride and Methocel E5 (hypromellose) at a ratio of 1:1 and 1:2 were dissolved in a solvent mixture of dichloromethane-methanol (1 to 1, v/v) and the solutions were dried to a residual solvent level of less than 1% (w/w). Analogously, 1:1 and 1:2 co-precipitates of lercanidipine hydrochloride and Kollidon VA 64 were prepared. Powder X-ray diffraction patterns were generated on all the four samples. XRD patterns for lercanidipine-Kollidon VA 64 solid solutions are shown in FIG. 5 demonstrating that the solid solution of lercanidipine HCl and Kollidon VA 64 at the ratio of 1:2 is almost totally amorphous.

Example 2

Turbidity Measurements

Figure 3:
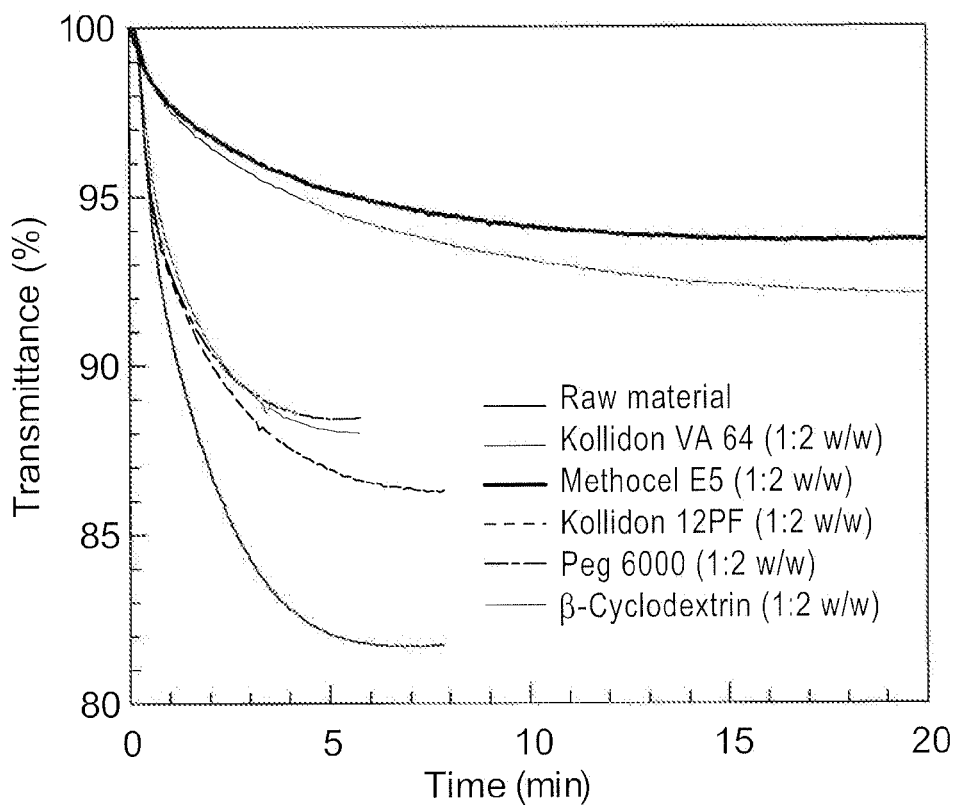
FIG. 3 illustrates the turbidity profiles for solid solutions/dispersions of (A) lercanidipine HCl and (B) nifedipine.
Figure 3:
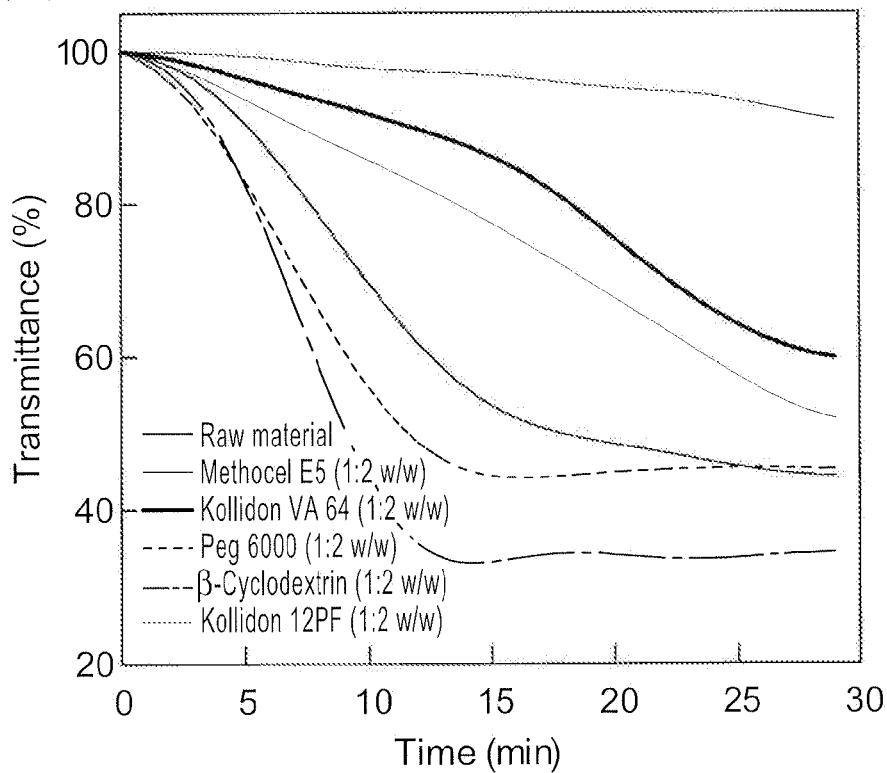

A concentrated solution (3 mL) of Nifedipine in acetone (0.5 mg/mL) was added to 200 mL of a buffer solution (pH 6.0) containing Kollidon VA 64, Methocel E5 (hypromellose), polyethylene glycol (PEG 6000), cyclodextrin or Kollidon 14 PF (polyvinyl pyrrolidone) at a nifedipine/polymer ratio of 1:2 by weight. The transmittance of the nifedipine/polymer solutions was monitored over time as shown in FIG. 3B. The more stable solutions exhibited a slower decline in transmittance over time, due to slower crystallization of nifedipine from solution. Methocel E5, Kollidon VA 64, and Kollidon 14 PF exhibited greater stabilization.

Powder X-Ray Diffraction

Figure 6:
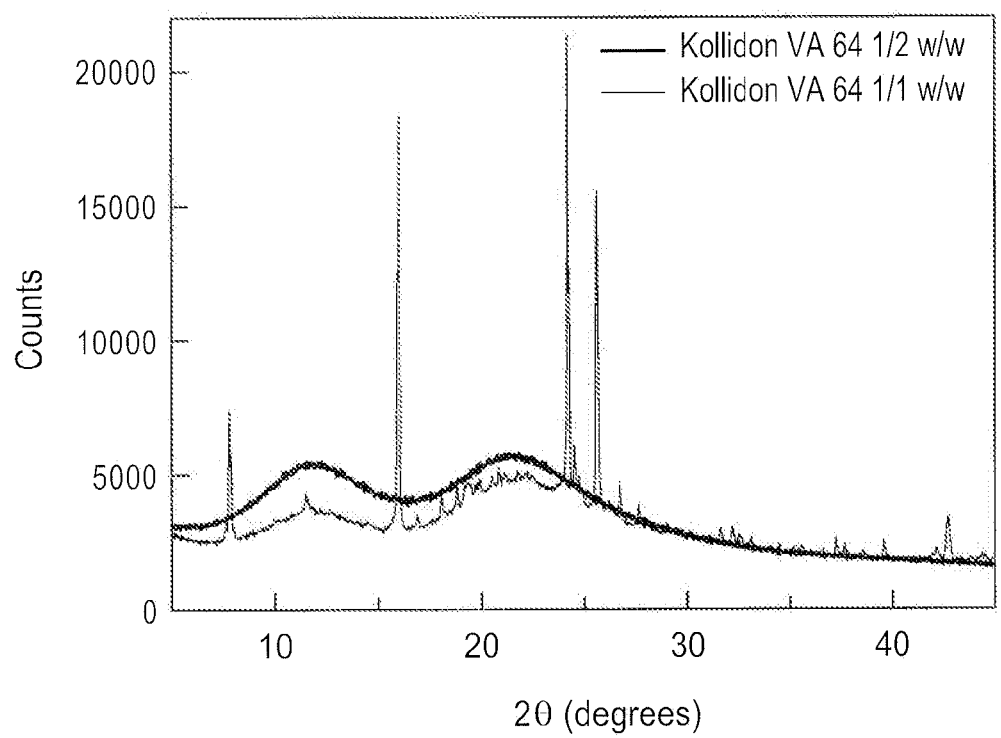
FIG. 6 illustrates the powder X-ray diffraction patterns of solid dispersions of nifedipine and (A) Kollidon VA 64 or (B) Methocel E5.
Figure 6:
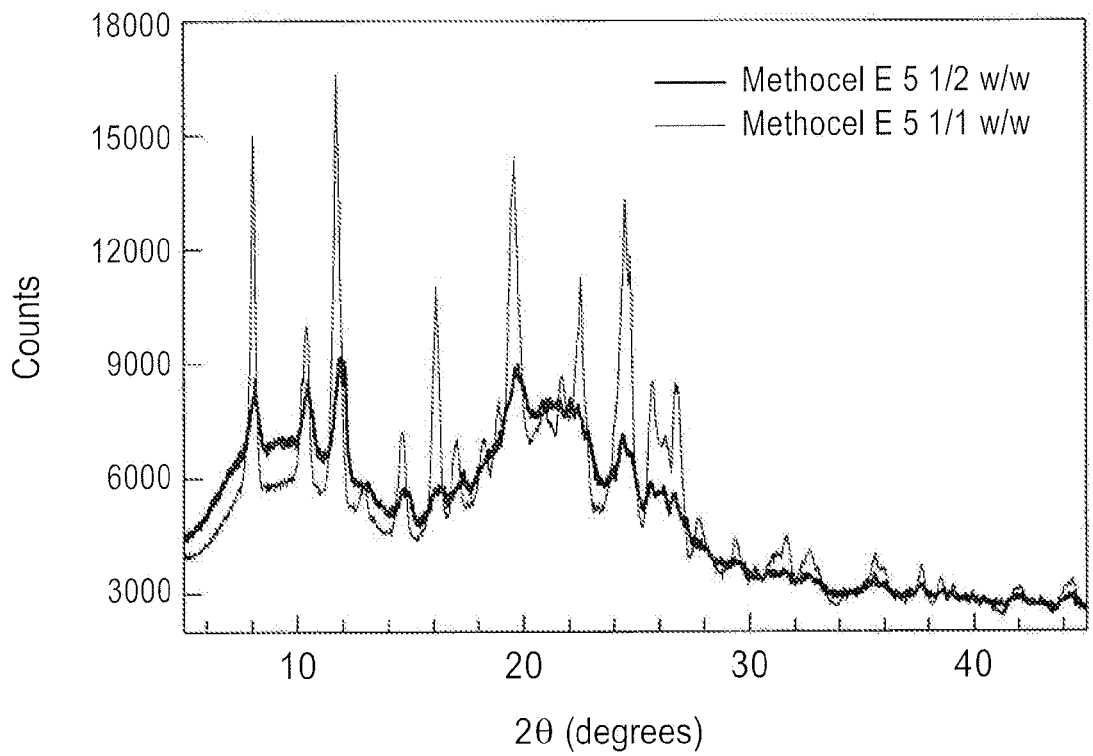

Two co-precipitates of nifedipine and Methocel E5 (hypromellose) were prepared at a nifedipine/Methocel ratio of 1:1 and 1:2 by dissolving the nifedipine and Methocel in a mixture of dichloromethane-methanol (1:1, v/v), then drying the solutions to a residual solvent level of less than 1% (w/w). Using the same method, 1:1 and 1:2 co-precipitates of nifedipine and Kollidon VA 64 were also prepared. All four samples were analyzed by powder X-ray diffraction; XRD patterns for nifedipine-Kollidon VA 64 solid solutions are shown in FIG. 6. The presence of sharp peaks in the XRD pattern for the 1:1 co-precipitate indicates that nifedipine present in crystalline form. The broad, relatively featureless XRD pattern of the 1:2 co-precipitate indicates that nifedipine is almost totally non-crystalline, and forms a solid dispersion in the Kollidon VA 64.

Example 3

3A—Nifedipine IR Beads (Nominal Nifedipine Loading: 10%)

Kollidon VA 64 (800 g) was slowly added to a 72.5/22.5/5 mixture of 95% ethanol/acetone/water (4930 g/1530 g/340 g) while vigorous stirring until dissolved, and then nifedipine (400 g) was slowly until dissolved. A Glatt GPCG 3 equipped with a 7" bottom spray/8" column height Wurster insert, 20 mm partition gap, air-distribution plate B (250 μm screen), 1.0 mm nozzle port, atomization air pressure of 1.5 bar, and 3.2 mm inner diameter tubing, was charged with 2584 g of 25-30 mesh Sugar Spheres. About 40 g of talc was homogenized into the nifedipine/polymer solution to minimize static build-up. The nifedipine solution, at a solids content of 15% by weight, was sprayed onto the sugar spheres at a spray rate of 8-17 g/min and outlet flap at ~60-80% (air velocity: ~85-115 m³/hr) while maintaining the product temperature at about 36-40° C. The resulting nifedipine-layered beads (batch size: 3724 g) were dried in the Glatt unit at 40° C. for about 45 min to minimize the residual solvent level in the product. A 98.5% yield of useable beads (600-1200 μm) was obtained.

2800 g of nifedipine-layered beads were provided with coating weight of 2% (i.e., weight of the coating relative to the weight of uncoated beads) protective seal-coat of Opadry® Clear (at 8% by weight solids; product temperature: 37-41° C.; spray rate: 5-12 g/min), and were further dried at 40° C. in the Glatt unit for about 45 min to drive off residual solvent/moisture. The measured potency was 9.81% (% nifedipine) compared to the target potency of 10% nifedipine.

3B—Nifedipine TPR Beads (TPR Coating: Eudragit RL/Eudragit L/TEC/Talc at a Ratio of 45/40/10/5)

Nifedipine IR beads (700 g) having a nominal drug loading of 10%, prepared as described above in 3A, were coated by spraying a 45/40/10/5 solution of Eudragit RL/Eudragit L/TEC/talc in 45/55 acetone/ethanol (the talc was suspended in the solution using an Ultraturrex homogenizer) at a solids content of 10% solids, to provide coatings of up to 20% by weight (samples were pulled at coating weights of 5%, 10%, and 15%).

The TPR coating solution was prepared by first slowly adding the Eudragit RL polymer to the solvent mixture to achieve a clear solution while stirring. Next, the Eudragit L polymer and then the plasticizer (triethylcitrate or "TEC") were slowly added and allowed to dissolve in the solution. Talc was separately homogenized in the solvent mixture before being added to the dissolved polymers and plasticizer. A Glatt GPCG 1 equipped with a 4" bottom spray Wurster insert, 20 mm partition gap, air-distribution plate B (250 μm screen), 1.0 mm nozzle port, atomization air pressure of 1.5 bar, and 3.2 mm inner-diameter tubing, and a T165P dedicated filter bag, was used to apply the TPR coating solution to the nifedipine IR beads. The TPR coating solution was sprayed at a spray rate of 4-11 g/min, outlet flap at ~20-30% (air velocity: ~2.0-2.5 m/s), and at a product temperature of 35-38° C. The coated beads were dried in the Glatt at 40° C. for 45 minutes to drive off excess residual solvents. The dried beads were sieved to discard any doubles (i.e., two or more beads adhered together by the TPR coating), if formed. TPR beads having coating weights of about 5% and 15% were assayed for potency and drug release profile using HPLC methodology.

3C—Nifedipine IR Beads (Nominal Nifedipine Loading: 5% by Weight)

Nifedipine IR beads having a nominal drug load of 5% by weight were prepared following the procedures described above in 3A. 190 g of nifedipine and 380 g of Kollidon VA 64 were layered on 3154 g of 25-30 mesh sugar spheres. The measured potency was determined to be 4.81% nifedipine (compared to the theoretical nominal potency of 5% nifedipine).

3D—Nifedipine TPR Beads (Coating: 40/45/10/5 Eudragit RL/L/TEC/Talc)

Nifedipine IR beads (700 g) having a nominal nifedipine loading of 5%, prepared as described in 3C above, were coated with a TPR coating solution of 45/40/10/5 Eudragit RL/Eudragit L/TEC/talc in a Glatt GPCG 1, following the procedures described in 3B above, at coating levels of 5%, 10%, 15% and 20% by weight. TPR beads having coating weights of about 5% and 15% were assayed for potency and drug release profile using HPLC methodology.

Example 4

4A—Nifedipine IR Beads (60-80 Mesh Sugar Spheres)

Nifedipine IR beads (nominal nifedipine loading: 10% by weight) were prepared by spraying a 1:2 solution of nifedipine/Kollidon VA 64 onto 60-80 mesh sugar spheres in a Glatt GPCG 3, following procedures similar to those described above in 3A.

4B—Nifedipine TPR Beads (TPR Coating: 35/50/10/5 Eudragit RL/Eudragit L/TEC/Talc)

Nifedipine IR beads (700 g) prepared as described above in 4A, were coated by spraying a 35/50/10/5 solution of Eudragit RL/Eudragit L/TEC/talc at a coating weight of 20%, in a Glatt GPCG 1, following the procedures described above in 3B, and were dried in the Glatt at 40° C. for 10 minutes to drive off excess residual solvent. The dried beads were sieved to discard any doubles, if formed. TPR beads having coating weights of 5%, 10% and 15% were assayed for potency and drug release profile using HPLC methodology.

4C—Nifedipine TPR Beads (TPR Coating: 40/45/10/5 Eudragit RL/Eudragit L/TEC/Talc)

Nifedipine IR beads (700 g), prepared as described above in 4A, were coated by spraying a 40/45/10/5 solution of Eudragit RL/Eudragit L/TEC/talc at a coating weight of 20% in a Glatt GPCG 1, following procedures similar to those described above in 3B.

4D—Nifedipine TPR Beads (TPR Coating: 45/40/10/5 Eudragit RL/Eudragit L/TEC/Talc)

Nifedipine IR beads (700 g) prepared as described above in 3B, were coated by spraying a 45/40/10/5 solution of Eudragit RL/Eudragit L/TEC/talc at coating weight of 20% in a Glatt GPCG 1, following procedures similar to those described above in 2A, and were dried in the Glatt at 40° C. for 10 minutes to drive off excess residual solvent. TPR beads having coating weights of 15% and 20% were assayed for potency and drug release profile using HPLC methodology.

Drug Release Profiles of Examples 3 and 4

Figure 7:
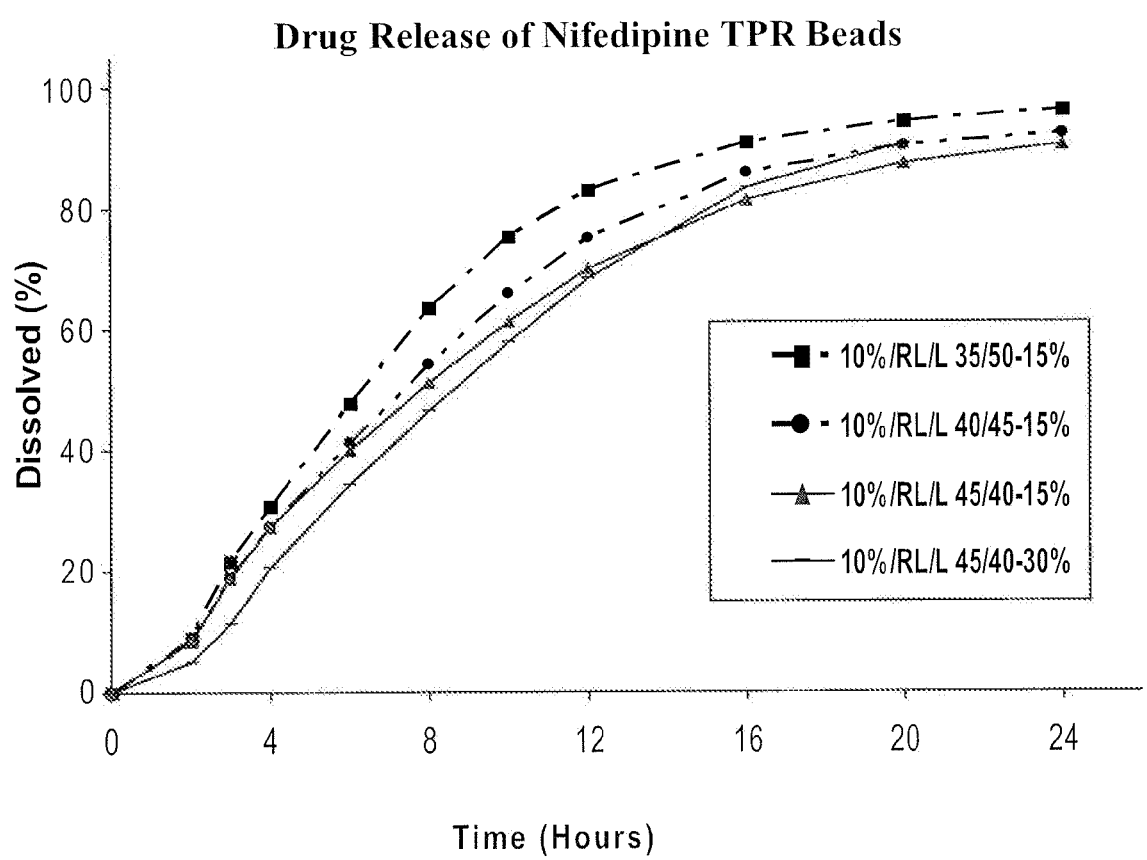
FIG. 7 illustrates the effect of the TPR coating composition on drug release from TPR beads described in Example 4.
Figure 8:
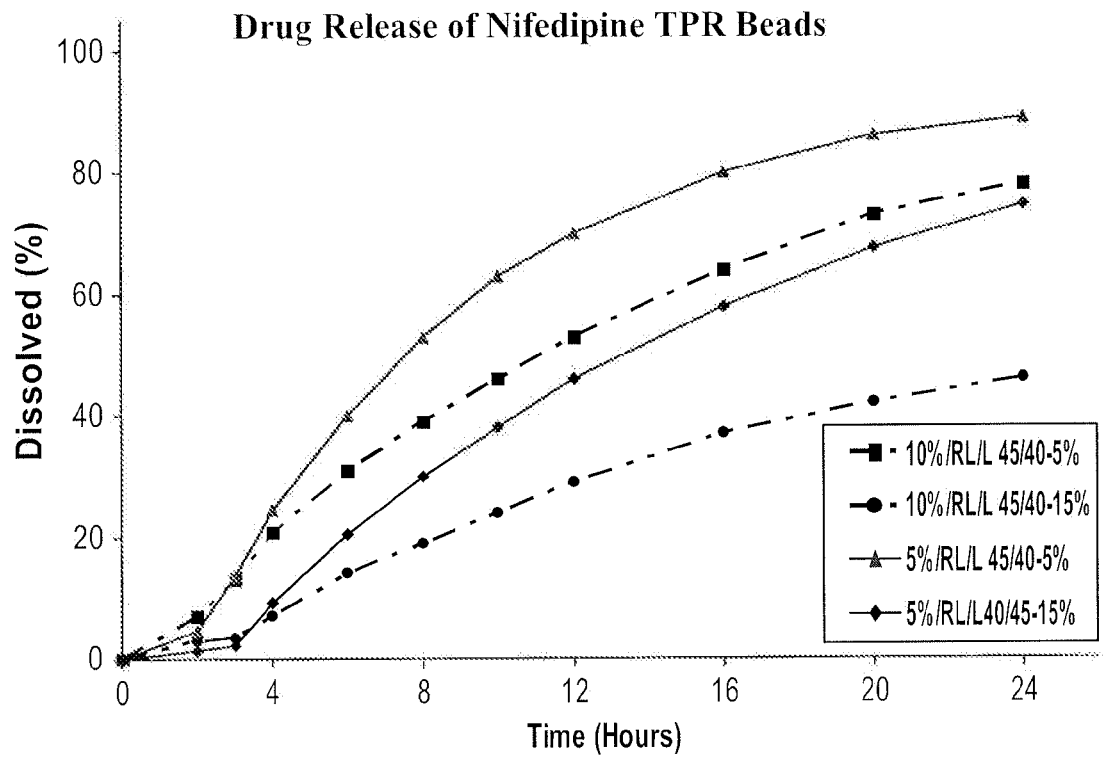
FIG. 8 illustrates the effect of drug loading on drug release from TPR beads (i.e., at 10% drug load versus 5% drug load) described in Example 3.
Figure 9:
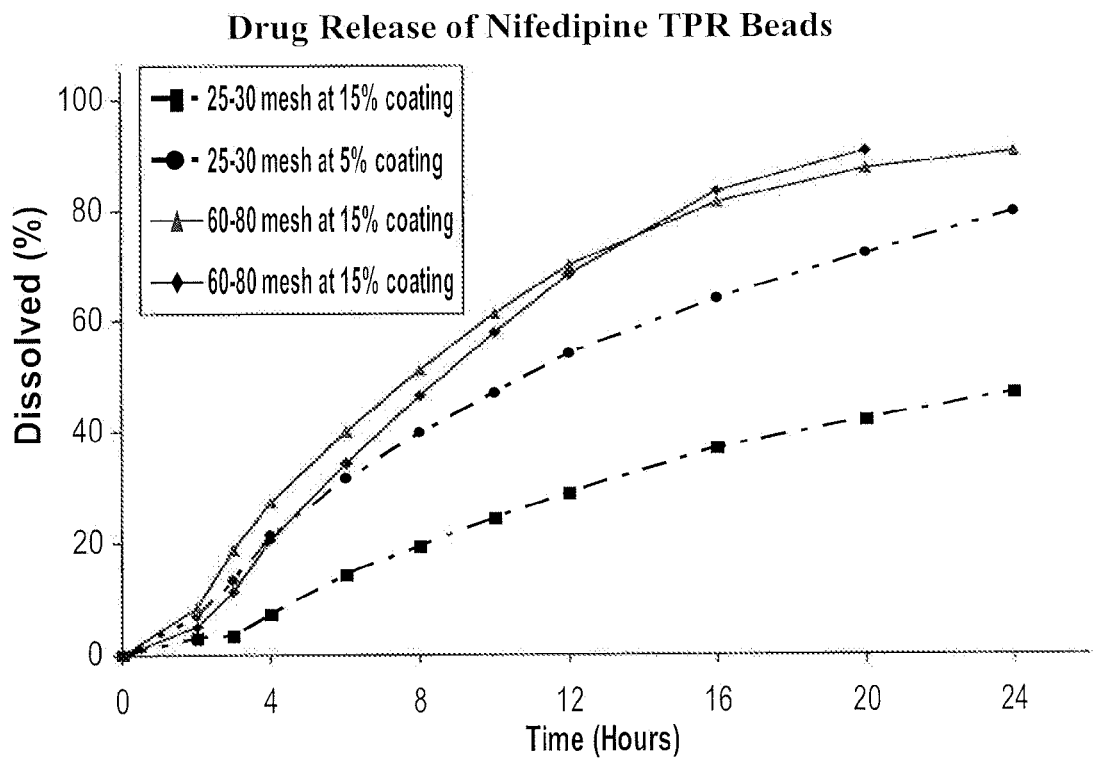
FIG. 9 illustrates the effect of the particle size on drug release from TPR beads coated at 10% drug load and 15% by weight of Eudragit RL/L coating at 45/40 on 60-80 mesh sugar spheres of Example 3B, compared to similar TPR beads prepared from 25-30 mesh sugar spheres of Example 4D.

FIG. 7 shows the effect of the TPR coating compositions on the release of nifedipine from the TPR beads of Example 4. Increasing the enteric polymer content (Eudragit L) in the TPR coating increases the rate of nifedipine release. FIG. 8 shows the effect of nifedipine loading on nifedipine release from the TPR beads of Example 3. Increasing the nifedipine loading from 5% to 10% lowers the rate of nifedipine release. FIG. 9 shows the effect of the particle size on drug release from TPR beads of Example 3B and 4D (25-30 mesh or 600-700 and 60-80 mesh or 170-250 μm, respectively) at the same TPR coating composition and coating weight. The smaller beads of example 4D show faster nifedipine release.

Example 5

5A—Model Drug IR Beads (Drug Loading: 10%)

Povidone (PVP K29/32, 128.2 g) was slowly added to 72.5/22.5/5 95% ethanol/acetone/water at 6% solids, with vigorous stirring until dissolved, then a weakly basic analog of lamotrigine (128.2 g) was slowly added until dissolved. A Glatt GPCG 3 equipped with a 6" bottom spray/8" column height Wurster insert, 20 mm partition gap, air-distribution plate D (200 mesh screen), 1.0 mm nozzle port, atomization air pressure of 1.0 bar, and 14 mm single-head tubing was charged with 1000 g of 25-30 mesh Sugar Spheres (Chris Hansen). The sugar spheres were coated with the drug solution at a spray rate of 8 mL/min, an outlet flap at 28-30% (air velocity: 3.6-4.2 m/s/pressure: 10.5-8 Pa), while maintaining the product temperature at about 32.5-33.5° C. The drug-layered beads were then coated with a protective seal-coat of Pharmacoat 603 at a coating weight of 2% and dried in the Glatt unit for about 10 min to drive off residual solvent/moisture. The coated beads were then sieved through 20-30 mesh screens.

5B—Model Drug TPR Beads (TPR Coating: 50/35/15 EC-10/HP-55/TEC)

The IR beads (1000 g), prepared as described above in 4A, were coated by spraying a solution of 50/35/15 EC-10/HP-55/TEC dissolved in 90/10 acetone/water (7400/822.2; 7.5% solids) at a coating weight of up to 40% by weight (samples were pulled at coating levels of about 20%, 25%, 30% and 35%). EC-10 (ethylcellulose, Ethocel Premium 10 cps from Dow Chemicals, 333.3 g) was slowly added to 90/10 acetone/water with continuous agitation for not less than 30 minutes, until dissolved. Then HP-55 (hydroxypropyl methylcellulose from Shin Etsu, 233.3 g) and TEC (100 g) were added to the EC-10 solution until dissolved. The TPR coating solution was applied with a Glatt GPCG 3 equipped with a 6" bottom spray/8" column height Wurster insert, 20 mm partition gap, air-distribution plate D (200 mesh screen), 0.8 mm nozzle port, atomization air pressure of 1.0 bar, and 14 mm single-head tubing, PB 3% dedicated filter bag. The TPR coating solution was sprayed onto the IR beads at a spray rate of 10-15 mL/min, outlet flap at about 28% (air velocity: 3.4-3.8 m/s/pressure: 7-7.5 Pa), while maintaining the product temperature at about 32-34° C., and dried in the Glatt at the same temperature for 10 minutes to drive off excess residual solvent. The dried beads were sieved to discard any doubles if formed.

5C—Model Drug TPR Beads (Coating: 35/50/15 EC-10/HP-55/TEC)

The IR beads (1000 g), prepared as described above in 5A, were coated with a 35/50/15 EC-10/HP-55/TEC TPR coating solution at a coating weight of 20%, 25%, 30%, 35%, and 40%, following procedures similar to those described above.

5D—Model Drug TPR Beads (Coating: 60/25/15 EC-10/HP-55/TEC)

The IR beads (1000 g), prepared as described above in 4A, were coated with a 60/25/15 EC-10/HP-55/TEC TPR coating solution at a coating weight of 5%, 10%, 15%, and 20%, following procedures similar to those described above.

Figure 10:
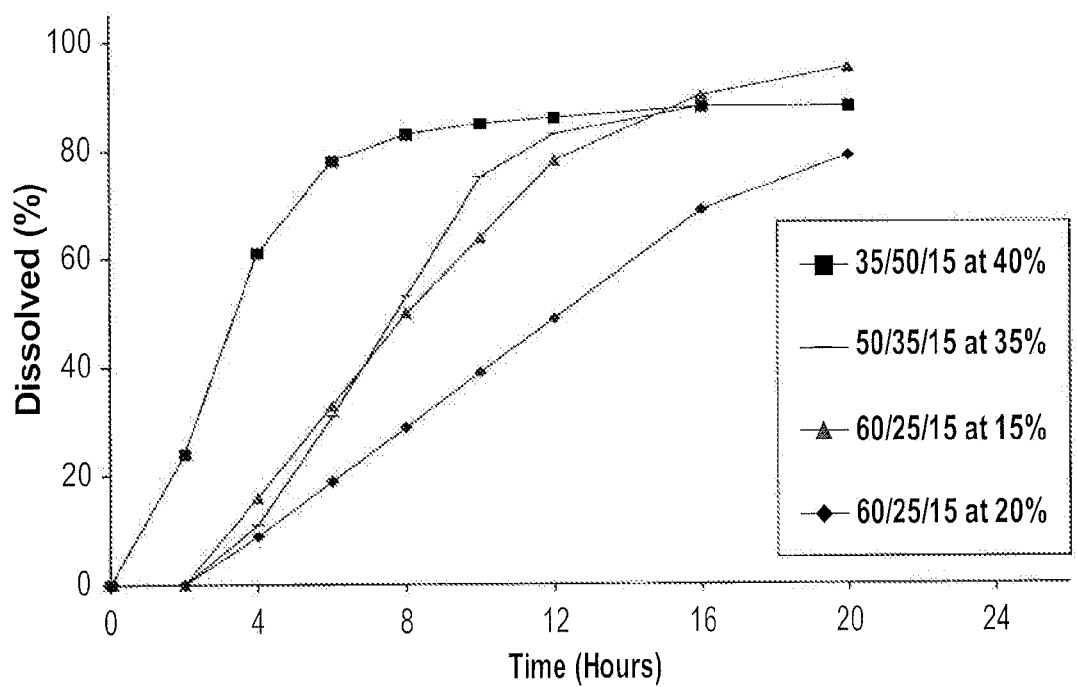
FIG. 10 illustrates the effect of TPR coating composition on drug release from the TPR beads of Example 5.

FIG. 10 shows the effect of the coating composition and/or coating level on the drug release from TPR beads at the same drug load of Example 5. Increasing the enteric polymer content in the TPR coating from 25% by weight to 50% by weight results in a significant increase in the rate of drug release from TPR beads.

Example 6

6A—Nifedipine IR Beads (Nifedipine/VA 64/Fumaric Acid)

Nifedipine IR beads were prepared by layering a 1/2/1 solution of Nifedipine/VA 64/fumaric acid dissolved in ethanol/acetone/water, onto 25-30 mesh sugar spheres in a Glatt GPCG 3, and a nominal nifedipine loading of 10% by weight, using procedures similar to those described above.

6B—Nifedipine IR Beads (Coating: Eudragit RL/L/TEC/Talc)

IR beads (700 g), prepared as described in 6A above, were coated with a 35/50/10/5 Eudragit RL/Eudragit L/TEC/talc TPR coating at a coating weight of up to 30% (samples were pulled at a coating level of 10%, 15%, 20%, and 25%), using procedures similar to those described above. TPR beads having coating weights of 15% and 20% were assayed for potency and drug release profile using HPLC methodology.

6C—Nifedipine TPR Beads (Dual Coating)

IR beads (700 g), prepared as described in 6A above, were coated in the fluid bed coater, GPCG 1, with an inner enteric coating layer comprising 85/10/5 Eudragit L/TEC/talc at a coating weight of 10%. Eudragit L100 was slowly added to ethanol vigorous stirring until dissolved, about 90 minutes. Then TEC (triethyl citrate) was slowly added to the solution until dissolved, followed by the addition, with constant stirring, of suspended talc. These enteric coated beads were then coated with a TPR layer of 35/50/10/5 Eudragit RL/Eudragit L/TEC/talc at coating weight of up to 30% (samples were pulled at a coating level of 10%, 15%, 20%, and 25%). Each layer was applied using procedures and processing conditions similar to those described above. TPR beads having TPR coating weights of 15% and 20% were assayed for potency and drug release profile using HPLC methodology.

Example 7

7A—Nifedipine IR Beads (Nifedipine/VA 64/Aspartic Acid)

Nifedipine IR beads were prepared by coating a 1/2/1 solution of Nifedipine/VA 64/aspartic acid in 72.5/22.5/5 ethanol/acetone/water onto 25-30 mesh sugar spheres in a Glatt GPCG 3, using procedure similar to those described above, to provide a nominal nifedipine loading of 10% by weight. Because aspartic acid was not soluble in the coating solution, it was homogenized in the coating solvent using an Ultraturrex homogenizer, before being added to the solution of nifedipine and Kollidon VA 64, and further homogenized.

7B—Nifedipine TPR Beads (Coating 35/50/15 RL/L-55/TEC)

Nifedipine IR beads (700 g), prepared as described in 7A above, were coated with 35/50/10/5 Eudragit RL/Eudragit L/TEC/talc at a coating weight of up to 30% (samples were pulled at a coating level of 10%, 15%, 20%, and 25%) using procedures similar to those described above. In TPR beads having coating weights of 15% and 20% were assayed for potency and drug release profile by HPLC methodology.

Example 8

8A—Lercanidipine HCl IR Beads (Lercanidipine/VA 64/Tartaric Acid)

Lercanidipine HCl (93 g) was slowly added to ethanol (4808 g), and stirred until dissolved. Kollidon VA 64 (186 g) followed by tartaric acid (21 g) were then slowly added until dissolved. A Glatt GPCG 1 equipped with a 6" bottom spray column height Wurster insert, 200 mm partition gap, air-distribution plate C (50 mesh screen), 0.8 mm nozzle port, atomization air pressure of 1.5 bar, was charged with 2100 g of 30-35 mesh Sugar Spheres (2322 g). The Sugar Spheres were coated with the lercanidipine/VA 64/tartaric acid coating solution by spraying at a spray rate of 11 g/min, outlet flap at 45-50% (air flow: 90-105 m$^3$/h), while maintaining the product temperature at about 32-34° C. The lercanidipine-layered beads were coated with a protective seal coat of Opadry Clear at a coating weight of 2%, and dried in the Glatt unit for about 15 min at 45° C. to drive off residual solvent/moisture, then sieved through 25 mesh screens.

8B—Lercanidipine TPR Beads (Coating: EC-10/HP-55/DEP at 1:4:1)

Lercanidipine HCl IR beads (930 g), prepared as described in 8A above, were coated by spraying the IR beads in a Glatt fluid granulator with a 1/4/1 solution of EC-10/HP-55/DEP in 98/2 acetone/water, at a coating weight of 27%, using procedures similar to those described above. The composition of the resulting TPR coating was 16.4% EC-10, 65.6% HP-55, 18% DEP (diethyl phthalate).

8C—Lercanidipine TPR Beads (Dual Layer Coating)

Eudragit L100 was slowly added to ethanol vigorous stirring until dissolved, about 90 minutes. Then TEC (triethyl citrate) was slowly added to the solution until dissolved, followed by the addition, with constant stirring, of suspended talc. An inner enteric coating of 74.1/7.4/18.5 Eudragit L100/TEC/talc, prepared as described above, was applied onto IR beads prepared as described in 8A above, at a coating weight of 20%. The resulting enteric-coated IR beads were then coated with a 16.4/65.6/18 EC-10/HP-55/DEP TPR coating solution to a coating weight of 10% using procedures similar to those described in 8B above.

8D—Lercanidipine TPR Beads (Triple Layer Coating)

Figure 11:
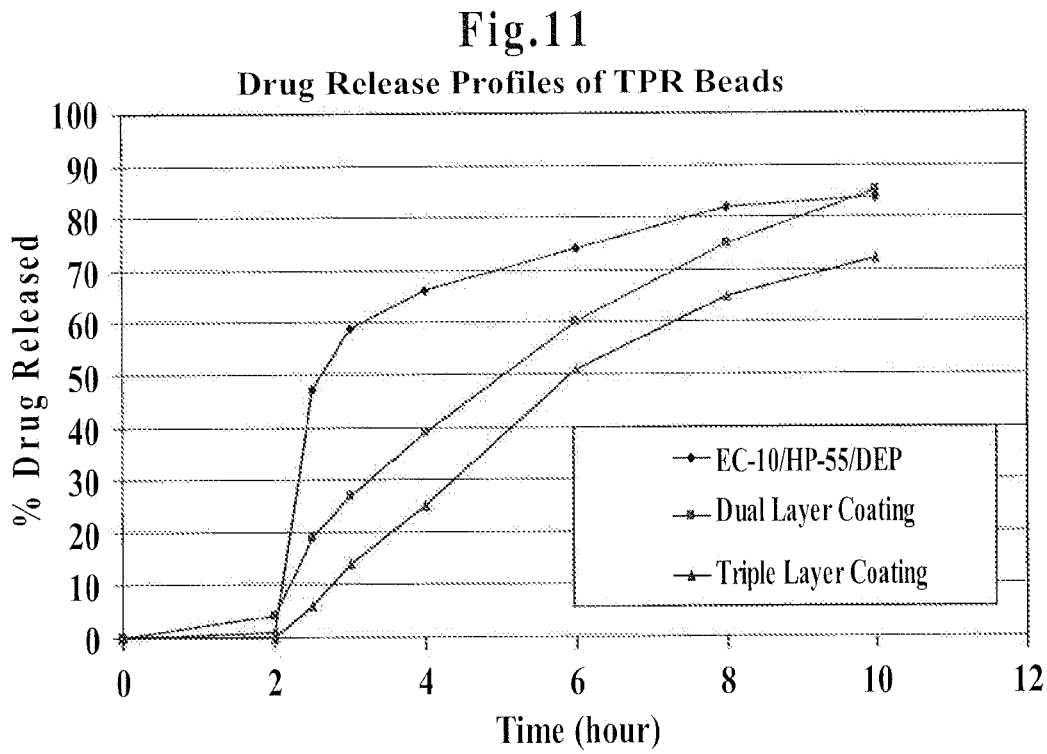
FIG. 11 illustrates the drug release profiles from Lercanidipine HCl TPR beads of Example 8 containing Kollidon VA 64 and tartaric acid.

An inner enteric coating of 80/20 HP-55/DEP was applied at a 20% coating weight onto IR beads prepared as described in 8A above, using procedures similar to those described above. The enteric-coated beads were then coated with a 16.4/65.6/18 EC-10/HP-55/DEP TPR coating solution to a coating weight of 25%, following procedures similar to those described above. These beads were then further coated with an outer enteric coating layer of Eudragit S100/TEC/talc at a ratio of 74.1/7.4/18.5 to a coating weight of 10% using procedures similar to those described above. The outer enteric coating layer was prepared by slowly adding Eudragit S100 to ethanol with vigorous stirring until dissolved, about 90 minutes. Then TEC (triethyl citrate) was slowly added to the Eudragit S100 until dissolved, followed by the addition, with constant stirring, of suspended talc. The drug-release profiles for TPR Beads of Examples 8B, 8C, and 8D were dissolution tested using a 2-stage methodology (i.e., first 2 hours in 0.1N HCl and 0.3% Tween 80, and subsequently at pH 6.8). The results of the dissolution testing are shown in FIG. 11.

Example 9

9A—Nifedipine IR Beads (Nifedipine/VA 64/Tartaric Acid)

Nifedipine IR beads were prepared by layering a 1/2/1 solution of nifedipine/VA 64/fumaric acid dissolved in ethanol/acetone/water onto 25-30 mesh sugar spheres in a Glatt GPCG 3, at a nominal nifedipine loading 10% by weight.

9B—Nifedipine TPR Beads (Coating 35/50/15 RL/L-55/TEC)

Nifedipine IR beads (1000 g), prepared as described in 9A above, were coated by spraying a solution of Ethocel Premium10 cps (EC-10), hypromellose phthalate (HP-55) and diethyl phthalate (DEP), dissolved in acetone/water, at coating weights of up to 30% (samples were pulled at a coating level of 10%, 15%, 20%, and 25%) in a Glatt fluid granulator, using procedures similar to those described above. The spraying solution had the following composition: 1.23% EC-10, 4.92% HP-55, 1.35% DEP; solvent: 90.65% acetone and 1.85% water.

Example 10

10A—IR Beads (Drug Load: 16.67%)

Povidone (PVP K29/32, 666.7 g) was slowly added to 16.6/83.4 ethanol/acetone with vigorous stirring until dissolved. Iloperidone (333.3 g), was slowly added until dissolved. 25-30 Mesh Sugar Spheres (1000 g) were then coated with the drug solution (8.17% solids) in a Glatt GPCG 3, using procedures similar to those described above. The drug-layered beads were coated with a protective sealcoat of Pharmacoat 603 at a coating weight of 2%. The IR beads were dried in the unit for about 10 min to drive off residual solvent/moisture and sieved to discard doubles if formed.

10B—TPR Beads (Dual Coating: 45/40/15 EC-10/HP-55/TEC over HP-55/TEC)

IR beads (1800 g), prepared as described in 10A above, were coated by spraying a 80/20 enteric coating solution of HP-55/TEC solution in 95/5 acetone/water at a coating weight of 8%. The enteric coated beads (850 g) were then coated with a 45/40/15 EC-10/HP-55/TEC TPR coating solution in 90/10 acetone/water mixture (7.5% solids) at a coating weight of up to 50% (samples were pulled at a coating level of 20%, 30%, and 40%) in a Glatt GPCG 3, using procedures similar to those described above, and dried in the Glatt at about 50° C. for 10 minutes to drive off excess residual solvent and sieved to discard any doubles if formed.

10C—TPR Beads (Dual Coating: 30/55/15 EC-10/HP-55/TEC over HP-55/TEC)

Figure 12:
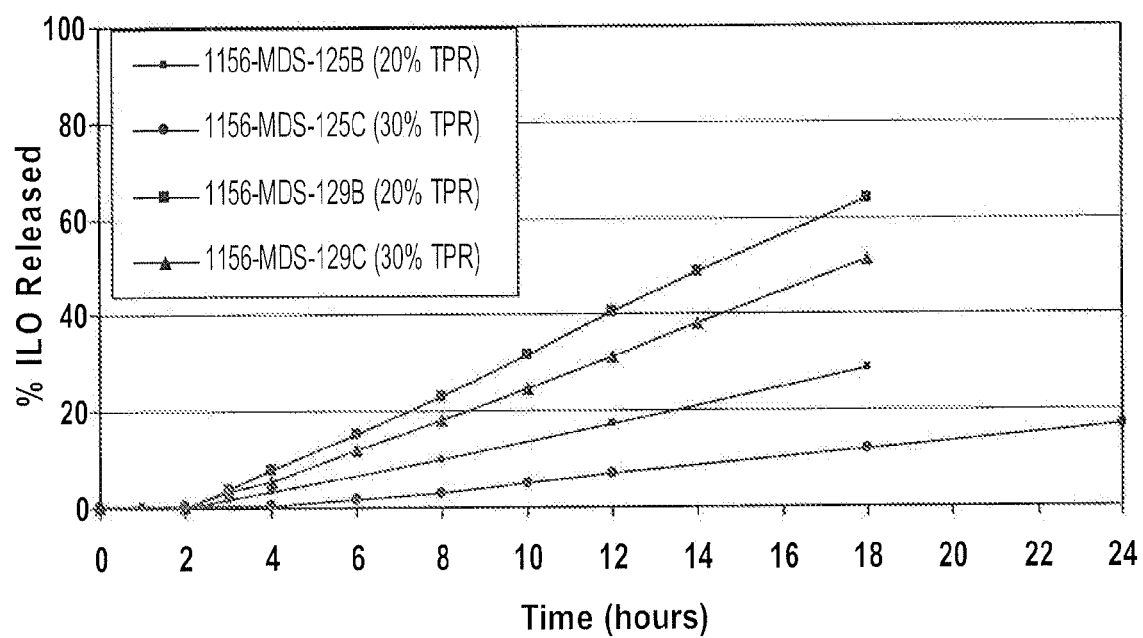
FIG. 12 illustrates the effects of TPR coating composition as well as thickness on the drug release from TPR beads of Example 9.

The enteric coated beads (530 g), prepared as described in 10B above, were coated by spraying with a 30/55/15 EC-10/HP-55/TEC TPR coating solution in 90/10 acetone/water (7.5% solids) at a coating weight of up to 50% (samples were pulled at a coating level of 20%, 30%, and 40%) in a Glatt GPCG 3, using procedures similar to those described above. Representative drug release profiles from TPR beads coated at two different TPR compositions/levels are shown in FIG. 12.

What is claimed is:

1. A pharmaceutical composition comprising timed pulsatile release (TPR) beads and rapidly dispersing microgranules wherein said TPR beads comprise:
   a solid dispersion of at least one active pharmaceutical ingredient in at least one solubility-enhancing polymer wherein the active pharmaceutical ingredient comprises a weakly basic active pharmaceutical ingredient having a solubility of not more than 100 µg/mL at pH 6.8;
   a TPR coating comprising a water insoluble polymer and an enteric polymer;
   said rapidly dispersing microgranules comprising particles of at least one disintegrant, and a sugar alcohol and/or saccharide, wherein said particles of the disintegrant and sugar alcohol and/or saccharide have an average particle size of not more than 30 µg/mL;
   wherein the average particle size of the TPR beads and rapidly dispersing microgranules is not more than 400 µg/mL; and
   wherein the composition provides a therapeutically effective plasma concentration of the active pharmaceutical ingredient over a period of at least about 18 hours.

2. The pharmaceutical composition of claim 1, wherein the ratio of water-insoluble polymer to enteric polymer in the TPR coating ranges from about 9:1 to about 1:9.

3. The pharmaceutical dosage form of claim 2, wherein the TPR coating further comprises about 3% to about 30% by weight of a plasticizer (compared to the total weight of the TPR coating).

4. The pharmaceutical composition of claim 1, wherein the solid dispersion of the active pharmaceutical ingredient and solubility-enhancing polymer is deposited on an inert core.

5. The pharmaceutical composition of claim 4, wherein the solubility-enhancing polymer is selected from the group consisting of polyvinylpyrrolidone, vinyl acetate/vinyl pyrrolidone copolymers, methylcellulose, hydroxypropyl cellulose, hydroxypropyl methylcellulose, polyethylene oxide, polyethylene glycol, and cyclodextrins.

6. The pharmaceutical composition of claim 4, wherein the solid dispersion further comprises a pharmaceutically acceptable organic acid.

7. The pharmaceutical composition of claim 6, wherein the ratio of organic acid to active pharmaceutical ingredient ranges from about 4/1 to about 1/9 by weight.

8. The pharmaceutical composition of claim 4, wherein the water-insoluble polymer is selected from the group consisting of polymers or copolymers of methacrylic acid esters having quaternary ammonium groups, polyvinyl acetate polymers or copolymers, cellulose acetate, cellulose acetate butyrate, ethyl cellulose, and mixtures thereof.

9. The pharmaceutical composition of claim 4, wherein the TPR beads comprise IR beads coated with the TPR coating; and
   the IR beads comprise inert cores coated with the solid dispersion.

10. The pharmaceutical composition of claim 9, wherein the ratio of active pharmaceutical ingredient to solubility-enhancing polymer ranges from about 6:1 to about 1:9.

11. The pharmaceutical composition of claim 9, wherein the TPR beads further comprise an enteric coating applied over the solid dispersion;
   the enteric coating is up to about 40% of the total weight of the TPR beads; and
   the TPR beads provide a lag time of about 1-4 hours.

12. The pharmaceutical composition of claim 9, wherein the TPR beads further comprise an enteric coating applied over the TPR coating;
   the enteric coating is up to about 40% of the total weight of the TPR beads; and
   the TPR beads provide a lag time of up to about 4 hours.

13. The pharmaceutical composition of claim 9, wherein the TPR beads further comprise a first enteric coating applied over the solid dispersion; and
   a second enteric coating applied over the TPR coating;
   the first and second enteric coatings are each up to about 40% of the total weight of the TPR beads; and
   the TPR beads provide a lag time of up to about 4 hours.

14. The pharmaceutical composition of claim 10, comprising a combination of IR and TPR beads, wherein the ratio of IR to TPR beads is 1:9 to 5:5.

15. The pharmaceutical composition of claim 9 comprising TPR beads, rapidly dispersing microgranules, and IR beads, wherein the ratio of IR beads to TPR beads ranges from about 10:90 to about 50:50.

16. The pharmaceutical composition of claim 15, wherein the IR beads further comprise a taste-masking layer coated over the solid dispersion; and
   wherein the taste-masking layer comprises a water-insoluble polymer or a water-insoluble polymer in combination with a water-soluble or gastrosoluble pore former.

17. The pharmaceutical composition of claim 1, wherein the one or more active pharmaceutical ingredients are selected from the group consisting of analgesics, anticonvulsants, anti-diabetic agents, anti-infective agents, anti-neoplastic agents, anti-Parkinsonian agents, anti-rheumatic agents, cardiovascular agents, CNS (central nervous system) stimulants, dopamine receptor agonists, anti-emetics, gastrointestinal agents, psychotherapeutic agents, opioid agonists, opioid antagonists, anti-epileptic drugs, histamine H2 antagonists, anti-asthmatic agents, and skeletal muscle relaxants.

18. The pharmaceutical composition of claim 17, wherein the active pharmaceutical ingredient is lercanidipine, or pharmaceutically acceptable salts, solvates, and/or esters thereof.

19. The pharmaceutical composition of claim 15, wherein:
   the IR beads further comprise a seal coating comprising hypromellose applied over the solid dispersion;
   the solubility-enhancing polymer comprises a vinylpyrrolidone-vinyl acetate copolymer or polyvinyl pyrrolidone;
   the TPR coating comprises a pharmaceutically acceptable methacrylate ester/methylmethacrylate ester copolymer and a pH-sensitive methacrylic acid-methylmethacrylate copolymer at a ratio of 9:1 to 1:9;
   the weight of the TPR coating is up to about 50% of the weight of the TPR beads; and
   the active pharmaceutical ingredient is selected from the group consisting of nifedipine, nicorandil, lercanidipine, iloperidone, clonazepam, and pharmaceutically acceptable salts, solvates and/or esters thereof.

* * * * *

UNITED STATES PATENT AND TRADEMARK OFFICE
CERTIFICATE OF CORRECTION

PATENT NO. : 10,864,166 B2
APPLICATION NO. : 13/911961
DATED : December 15, 2020
INVENTOR(S) : Gopi Venkatesh et al.

It is certified that error appears in the above-identified patent and that said Letters Patent is hereby corrected as shown below:

In the Claims

Claim 1, Column 25, Line 17: please delete "µg/mL" and replace with --µm--

Claim 1, Column 25, Line 20: please delete "µg/mL" and replace with --µm--

Signed and Sealed this
Eleventh Day of April, 2023

Katherine Kelly Vidal
*Director of the United States Patent and Trademark Office*